United States Patent
Fiset

(10) Patent No.: US 7,921,853 B2
(45) Date of Patent: Apr. 12, 2011

(54) PHOTOTHERAPY METHOD FOR TREATING PSORIASIS

(75) Inventor: Peter Depew Fiset, Loudonville, NY (US)

(73) Assignee: LEDeep LLC, Loudonville, NY (US)

( * ) Notice: Subject to any disclaimer, the term of this patent is extended or adjusted under 35 U.S.C. 154(b) by 367 days.

(21) Appl. No.: 10/591,960

(22) PCT Filed: Mar. 9, 2005

(86) PCT No.: PCT/US2005/007708
§ 371 (c)(1),
(2), (4) Date: Jun. 25, 2007

(87) PCT Pub. No.: WO2005/086846
PCT Pub. Date: Sep. 22, 2005

(65) Prior Publication Data
US 2007/0276455 A1 Nov. 29, 2007

Related U.S. Application Data

(60) Provisional application No. 60/552,018, filed on Mar. 9, 2004.

(30) Foreign Application Priority Data

May 24, 2004 (WO) ............... PCT/US2004/014527
May 24, 2004 (WO) ............... PCT/US2004/016299

(51) Int. Cl.
*A61B 19/00* (2006.01)
*A61N 5/06* (2006.01)

(52) U.S. Cl. ............... 128/898; 607/88; 607/91; 607/94

(58) Field of Classification Search .............. 607/88–91, 607/93, 94; 128/898; 606/9
See application file for complete search history.

(56) References Cited

U.S. PATENT DOCUMENTS

| | | | |
|---|---|---|---|
| 4,309,616 A | 1/1982 | Wolff | |
| 4,469,102 A | 9/1984 | Fish | |
| 4,703,184 A | 10/1987 | Wolff | |
| 4,839,513 A | 6/1989 | Wijtsma | |
| 4,858,609 A | 8/1989 | Cole | |
| 5,374,825 A * | 12/1994 | Doty et al. | 250/372 |
| 5,601,619 A | 2/1997 | Dreschler | |
| 5,913,883 A | 6/1999 | Alexander et al. | |
| 6,084,250 A | 7/2000 | Jüstel et al. | |
| 6,207,229 B1 | 3/2001 | Bawendi et al. | |

(Continued)

FOREIGN PATENT DOCUMENTS

DE 198 52 524 A1 5/2000

(Continued)

OTHER PUBLICATIONS

Supplementary Partial European Search Report dated Dec. 7, 2009, in corresponding EP 04751757.8, 4 pages.

(Continued)

*Primary Examiner* — Ahmed M Farah
(74) *Attorney, Agent, or Firm* — Foley & Lardner LLP

(57) ABSTRACT

A system and method for phototherapy, including skin tanning, lupus phototherapy, teeth whitening, hair growth and psoriasis phototherapies are provided. The system (1) includes a chamber adapted for at least one type of phototherapy and at least one UV LED, at least one nanostructure UV light emitting device or a combination of UV LEDs and nanostructure light emitting devices.

7 Claims, 11 Drawing Sheets

U.S. PATENT DOCUMENTS

| | | |
|---|---|---|
| 6,290,713 B1 | 9/2001 | Russell |
| 6,322,901 B1 | 11/2001 | Bawendi et al. |
| 6,350,275 B1 | 2/2002 | Vreman et al. |
| 6,423,551 B1 | 7/2002 | Weiss et al. |
| 6,447,537 B1 | 9/2002 | Hartman |
| 6,452,217 B1 | 9/2002 | Wojnarowski et al. |
| 6,461,376 B1 | 10/2002 | Beshore |
| 6,494,900 B1 | 12/2002 | Salansky et al. |
| 6,515,314 B1 | 2/2003 | Duggal et al. |
| 6,585,947 B1 | 7/2003 | Nayfeh et al. |
| 6,596,016 B1 | 7/2003 | Vreman et al. |
| 6,602,275 B1 * | 8/2003 | Sullivan .......................... 607/88 |
| 6,616,447 B1 | 9/2003 | Rizoiu et al. |
| 6,621,211 B1 | 9/2003 | Srivastava et al. |
| 6,828,576 B2 | 12/2004 | Spivak |
| 6,861,658 B2 * | 3/2005 | Fiset .......................... 250/504 R |
| 6,906,463 B2 | 6/2005 | Hildenbrand et al. |
| 7,001,414 B2 | 2/2006 | Unvert et al. |
| 7,239,072 B2 | 7/2007 | Snijkers-Hendrickx et al. |
| 7,254,151 B2 * | 8/2007 | Lieber et al. ............... 372/44.01 |
| 7,294,417 B2 | 11/2007 | Ren et al. |
| 7,306,620 B2 | 12/2007 | Cumbie |
| 2001/0053856 A1 | 12/2001 | Leduc et al. |
| 2002/0074559 A1 | 6/2002 | Dowling et al. |
| 2002/0127224 A1 | 9/2002 | Chen |
| 2002/0161418 A1 | 10/2002 | Wilkens et al. |
| 2002/0173833 A1 | 11/2002 | Korman et al. |
| 2002/0183811 A1 * | 12/2002 | Irwin .............................. 607/94 |
| 2003/0003300 A1 | 1/2003 | Korgel et al. |
| 2003/0034486 A1 | 2/2003 | Korgel et al. |
| 2003/0044114 A1 | 3/2003 | Pelka |
| 2003/0044365 A1 | 3/2003 | Candau et al. |
| 2003/0045916 A1 | 3/2003 | Anderson et al. |
| 2003/0161795 A1 | 8/2003 | Tsuzuki et al. |
| 2003/0167080 A1 | 9/2003 | Hart et al. |
| 2003/0216795 A1 | 11/2003 | Harth et al. |
| 2004/0015214 A1 | 1/2004 | Simkin et al. |
| 2004/0036130 A1 | 2/2004 | Lee et al. |
| 2004/0075065 A1 | 4/2004 | Spivak |
| 2004/0076926 A1 | 4/2004 | Baughman |
| 2004/0175337 A1 | 9/2004 | Richard et al. |
| 2004/0252488 A1 | 12/2004 | Thurk |
| 2005/0042187 A1 | 2/2005 | Verma et al. |
| 2005/0187596 A1 | 8/2005 | Fiset |
| 2005/0201963 A1 | 9/2005 | Dutta |
| 2006/0155349 A1 | 7/2006 | Kemeny et al. |
| 2006/0273328 A1 | 12/2006 | Niu et al. |
| 2007/0274909 A1 | 11/2007 | Justel et al. |
| 2008/0039907 A1 | 2/2008 | Fiset |
| 2009/0057650 A1 | 3/2009 | Lieber et al. |

FOREIGN PATENT DOCUMENTS

| | | |
|---|---|---|
| EP | 1 197 478 A1 | 4/2002 |
| WO | WO 95/24888 A1 | 9/1995 |

OTHER PUBLICATIONS

Supplementary European Search Report dated Dec. 17, 2009, in corresponding EP 05751907.6, 5 pages.

Green et al., "311 nm UVB phototherapy—an effective treatment for psoriasis," British Journal of Dermatology, Dec. 1, 1988, 119(6):691-696.

Ozawa et al., "312-nanometer Ultraviolet B Light (Narrow-Band UVB) Induces Apoptosis of T Cells within Psoriatic Lesions," J. Exp. Med., Feb. 15, 1999, 189(4):711-718.

Wang et al., "Multilayer waveguide-grating filters," Applied Optics, May 10, 1995, 34(14):2414-2420.

U.S. Appl. No. 10/558,092, filed Apr. 24, 2004, Fiset, Peter D.

\* cited by examiner

PHOTOTHERAPY METHOD FOR TREATING PSORIASIS

CROSS-REFERENCE TO RELATED APPLICATIONS

The present application claims benefit of U.S. Provisional Patent Application Ser. No. 60/552,018, filed Mar. 9, 2004; PCT Patent Application Number PCT/US2004/014527, filed May 24, 2004; PCT Patent Application Number PCT/US2004/016299, filed May 24, 2004, which are incorporated by reference in their entirety.

FIELD OF THE INVENTION

The present invention is directed generally to phototherapy systems and specifically to systems for treating lupus and psoriasis, for whitening teeth and for inducing hair growth.

BACKGROUND

The most common method of skin tanning involves the process of exposing skin to ultra-violet light. Health research has shown that both the condition of under-exposure to ultra-violet light and the condition of over-exposure to ultra-violet light causes a variety of health problems. Health research has also shown that specific ranges of wavelengths of ultra-violet light are responsible for producing health benefits. Moderate exposure to specific wavelengths of ultra-violet light produces the greatest benefits with the least amount of health risk. Certain methods and devices are useful at controlling the quantity and quality of ultra-violet light exposure in the effort to produce the greatest health benefits with the least amount of health risks. Ultra-violet light quality depends primarily on the ranges of wavelength of ultra-violet light; where the highest ultra-violet light quality is the ultra-violet light that produces the greatest net health benefits.

The sun is a primary source of ultra-violet light for tanning. The quantity of light exposure to the sun is simple to control. The quality of ultra-violet light exposure by the sun is not simple to control. Lamps that provide alternative sources of ultra-violet light allow for tanning services that do not rely on the sun. These tanning services are available and are administered in a controlled environment such as in personal care service salons. The industry providing controlled exposure to artificial ultra-violet light is generally referred to as the "indoor-tanning" industry. Indoor-tanning does not implement systems that are directly dependent on the sun as the source of ultra-violet radiation. The quality of the indoor-tanning ultra-violet light has become important in differentiating services available within the same indoor-tanning salon and between competing tanning salons.

Light with wavelengths in the ultra-violet range is often referred to as UV light or UV. UVA, UVB and UVC describe three separate non-overlapping but adjacent ranges of light fully encompassing the UV light range. The range of light referred to as UVA generally has the longest set of wavelengths within the UV range and includes wavelengths between 290 and 400. UVA-1 is between 340 and 400; UVA-2 is between 290 and 340; and UVA-3 is between 290 and 310. The range of light referred to as UVC generally has the shortest set of wavelengths within the UV range and includes wavelengths between 160 and 260. The range of light referred to as UVB includes wavelengths between 260 and 290.

The use of the terms UVA, UVB and UVC allow the various properties of UV light to be categorized in general ways. UVA has the best capability of tanning skin. UVB does not produce a tan in the third layer of skin. UVC light does not produce a tan but can sterilize some biological agents such as certain bacteria. Under certain conditions UVB will tan the second layer of skin. The second layer of skin when tanned with UVB has a shedding period of 5 to 8 days. Skin tanned with UVA only has the third layer of skin tanned which results in a normal shedding cycle of 28 days.

A light therapy is a method of applying a specific set of wavelengths of electromagnetic radiation in specific states and under specific conditions to produce a change in a bodily function. Tanning is a light therapy whereby the biological change is the production of melanin within the cells of the skin. Indoor-tanning is a light therapy utilizing the exposure of moderate amounts of UV over a reasonable amount of time to skin from UV sources other than the sun.

Under normal conditions the outer layer of skin, also known as the first layer, is composed of dead cells. Normally, dead cells will not produce melanin upon exposure to moderate amounts of UV. The layer under the first layer of skin is referred to as the second layer of skin, and is composed of active cells that may be functioning in some biological manner and will produce melanin upon exposure to UVB light. UVB skin tanning has, what some tanners consider, an additional negative effect, UVB tanning will thicken the second layer of skin and as a result increases the visibility of skin lines and wrinkles. UVB tanning creates a shedding cycle of 5 to 7 days which is undesirable when a UVA tan has a shedding cycle of 28 days. When UVB is combined with UVA the shedding cycle of the UVA tanned layer is accelerated since the second layer is shed more quickly and the third layer becomes the second layer as a result and is shed within another 5 to 7 days.

Under normal conditions the layer of skin that will produce melanin (melanogenesis) when exposed to UVA-3 or UVB light is referred to as the third layer of skin and more specifically the melanocytes within the skin. The Vitamin-D production is believed to be caused by exposure to UVA-3 or UVB light. However, UVB light can also degrade Vitamin-D. Since UVA-3 does not degrade Vitamin-D, UVA-3 is preferred over UVB for Vitamin-D production and melanogenesis. The selective elimination of UVB and selective production of UVA-1, UVA-2 and UVA-3 can be a benefit of the present invention. Melanogenesis is important for tanners who desire a darker tan than that which is obtained from UVA-1 or UVA-2 exposure alone. UVA-1 and UVA-2 converts melanin into the dark pigment melatonin. The Tanning Industry Association promotes a skin-type classification based on the amount of melanin present in the skin before additional melanin has been created by melanogenesis. These types include type I (little), II (low), III (moderate), IV (high) and V (black). In exceptional conditions such as albinism, the third layer of skin is not capable of producing melanin. For the purposes of this application, albino skin is considered an exception to the norm and will not be referred to as a third layer of skin but as an albino third layer of skin.

It is common knowledge that all wavelengths of UV over long exposure periods damages the skin in various ways. Therefore, it is desirable to limit the exposure of UV radiation to skin. Alternatively, some UV exposure is generally considered necessary in order to maintain good health in other bodily functions, such as the generation of vitamin-D. Vitamin-D is useful in the absorption of calcium in the body. Therefore, it has been recommended by various health organizations studying the phenomena that moderate exposure to UV light has a net health benefit, whereas over-exposure or under-exposure of UV results in a net health deficit. The art of indoor-tanning to remain useful should provide for ever increasing controllability of the application of the light therapy. As a light therapy tanning should be applied with specific goals and procedures to maximize the benefits of the therapy.

For people desiring a tan, the main benefits of UV exposure is the production of tanned skin. Tanners enjoy positive psychological and perceived positive social benefits resulting from having tanned skin. In order to limit the total amount of UV radiation tanners are exposed to while maintaining a tan, it is desirable to reduce as much as possible the exposure to UV light outside the UVA wavelength range. UVB and UVC wavelength ranges of radiation are by definition not capable of tanning skin with a 28 day shedding cycle and therefore reasonable efforts should be made to eliminate UVB and UVC from the source of light tanners are exposed to.

Indoor-tanning methods generate UV light from converting electrical energy to light within devices such as UV fluorescent bulbs and high and low pressure mercury vapor bulbs are two specific types of light bulb technologies. UV light bulbs currently in use have properties of high voltage, high temperature, and low electrical energy to UV conversion efficiencies under seventeen percent.

Within the fluorescent light bulb category there are a variety of types that differ mainly in the percentage of UV light produced in the UVA, UVB and UVC wavelength ranges. For tanners concerned with overexposure to UV light the more desirable fluorescent bulbs have a higher percentage of light in the UVA-1 wavelength range. Tanners concerned with overexposure prefer and tend to pay a premium for tanning services that have the least amount of UVB and UVC.

Depending on weather conditions, typically 88% of the UV radiation from the sun is UVA, in this case an artificial source with more than 88% of the UV radiation is UVA is considered a safer tanning method than sun-tanning. Common fluorescent tanning bulbs and associated services have UV composed between 92.0% UVA to 97.5% UVA. Currently, high pressure quartz metal-halogenide bulbs have in general 98.5% UVA and are considered to be the least harmful artificial tanning bulbs currently used in indoor-tanning salons.

BRIEF SUMMARY OF THE INVENTION

A preferred embodiment of the present invention provides a system for phototherapy, including skin tanning, lupus phototherapy, hair regrowth phototherapy, teeth whitening phototherapy and psoriasis phototherapy. The system comprises a chamber adapted for at least one of these phototherapies, and at least one light emitting diode emitting UV light, at least one nanostructure UV light emitting device, or a combination of one or more light emitting diode emitting UV light with one or more nanostructure UV light emitting devices.

Another preferred embodiment of the present invention provides a system for phototherapy, including skin tanning, lupus phototherapy, hair regrowth phototherapy, teeth whitening phototherapy and psoriasis phototherapy. The system comprises a first means for at least one of skin tanning and phototherapy, and at least one light emitting diode emitting UV light, at least one nanostructure UV light emitting device or a combination of one or more light emitting diode emitting UV light with one or more nanostructure UV light emitting devices.

Another preferred embodiment of the present invention provides a method for conducting phototherapy, including skin tanning, lupus phototherapy, hair regrowth phototherapy, teeth whitening phototherapy and psoriasis phototherapy. The method comprises providing UV light from at least one light emitting diode emitting UV light, at least one nanostructure UV light emitting device or a combination of one or more light emitting diode emitting UV light with one or more nanostructure UV light emitting devices onto a skin of a human subject who is located in a chamber adapted for at least one of these phototherapies in order to provide phototherapy for the skin.

For illustrative purposes, the devices, systems and methods of the present invention are sometimes described as including at least one light emitting diode that emits UV light or at least one nanostructure UV light emitting device. However, it should be understood that each of the embodiments described herein may be modified to include a combination of one or more light emitting diode emitting UV light with one or more nanostructure UV light emitting devices to provide a UV light source. In addition, each of these embodiments may be modified to include other light sources including, but not limited to, visible LEDs, infrared LEDs, fluorescent bulbs, mercury vapor based bulbs and combinations thereof in order to provide a desired spectral distribution for a given phototherapy application or for general lighting applications.

Unless otherwise noted, any values for wavelengths in this disclosure are provided in nanometers (nm).

DETAILED DESCRIPTION OF THE PREFERRED EMBODIMENTS

Figure 1:
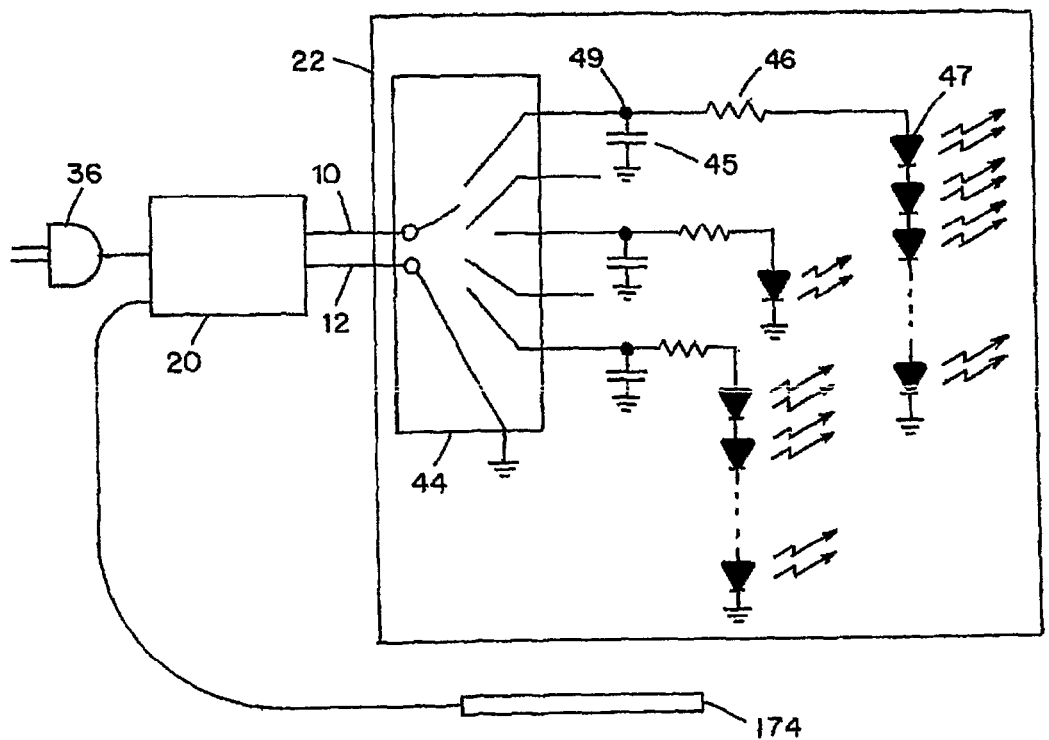
FIG. 1 shows an electrical schematic diagram for powering the LEDs. Also shown is a variable power supply which charges capacitors in a selective manner.

Some aspects of the present invention provide systems, devices and methods for use in phototherapies and in general purpose lighting applications. The systems and devices are based on UV emitting LEDs, UV emitting nanostructures, or a combination of the two. The use of UV emitting LEDs and/or UV emitting nanostructures provides a significant advantage over other UV phototherapy and lighting systems and devices because they make it possible to adjust the width and the wavelength range of the emission spectrum. For example, the present systems and devices may by tuned to provide emission bands having single or multiple peaks or combinations of both. The systems and devices may provide continuous emission spectra or discrete emission lines, or a combination of both. Both the amplitudes and full width half maximum of the bands can be adjusted, resulting in spectral densities which can be manipulated and programmatically controlled to vary during a phototherapy session in order to increase the effectiveness of the phototherapy.

UV LED-Based Phototherapy

A first aspect of the present invention incorporates the use of light emitting diodes, commonly referred to as LEDs, into a phototherapy device that optionally includes other sources of therapeutic electromagnetic radiation. In some embodiments, for example, where the device is used in tanning or for the treatment of lupus, UVA LEDs are preferred. Particularly preferred UVA LEDs include those that emit at least about 90% UVA wavelengths, preferably at least about 95% or more UVA wavelengths. In one embodiment, the LED emits essentially only (e.g., at least about 99.99%) UVA. The various LED manufacturers of the preferred LEDs are Cree Inc. (USA), Nichia (Japan), Toyoda Gosei (Japan), Crystal IS (USA-Aluminum Nitride AlN substrate) with Palo Alto Research Center (USA).

For providing some phototherapies other than or in addition to tanning and lupus therapy, it may be desirable to include LEDs that have different wavelengths instead of or in addition to UVA, such as UVB, UVC, violet and blue. Therefore in some of the present systems provide a mix of various wavelength LEDs that are incorporated in combinations that suit a particular therapy requirement. A light therapy device composed of UVA LEDs and other LEDs and other types of light bulbs is desirable to provide a variety of desired therapeutic effects. When the desired effect is tanning skin or lupus therapy then a portion of the LEDs are of the UVA LED variety. In general, UVA LEDs are used in combination with other light sources to produce a combination light therapy in a selectable and controllable manner. Light therapy devices with multiple and varied types of lamps include selectable power supplies that control how and when the various lamps are powered. Some devices, such as those for use in teeth whitening, hair regrowth and psoriasis therapies, may be designed with selectively controllable UVA LEDs such that they provide selectable treatment areas (e.g., on the teeth, scalp or area of psoriasis) and reduced power when treatment is not required at various points within the chamber.

There are many advantages of LEDs over light bulbs. LEDs are more efficient at converting electrical energy into directed light than many other UV light bulb types. LEDs do not require surfaces operating at high temperatures and can be safer. LEDs do not require high voltages or high currents to operate and, for this reason, LEDs are safer and require less structure to protect the people in proximity to the light source. Additionally, LEDs can be smaller than light bulbs. As discrete components LEDs may be fabricated as arrays in a wide variety of shapes and form factors, including a fluorescent bulb form factor, an industry standard light bulb, or an industry standard spot light bulb.

In a fluorescent bulb form factor the UV LED arrays can contain an internal power conversion or external power conversion (or a combination of internal and external power conversion) and directly replace a UV fluorescent bulb in currently installed tanning devices currently made for indoor-tanning devices. In this manner, conventional tanning devices may be readily converted into phototherapy devices for a range of treatments, including teeth whitening, hair regrowth and psoriasis therapies. Current indoor-tanning devices for the prone body position are commonly referred to as tanning beds. Current indoor-tanning devices for upright body positions are commonly referred to as tanning booths. Collectively, tanning booths and tanning beds are referred to as tanning chambers.

In ideal conditions, UV LED semiconductor chips have a lifetime on the order of 100,000 hours. Encapsulated LEDs have an epoxy or plastic encapsulation. The encapsulated UV LEDs have an effective lifetime of 10,000 hours due to degradation of the encapsulation material from UV exposure. The chips within the encapsulation continue to operate past the 10,000 hours but the UV degraded encapsulation material does not allow as much UV light to escape. In order to maintain a calibrated constant total radiant flux per tanning session over the life of the encapsulated UV LED based phototherapy device, then either, the corrective action of increasing the electric current supplied to the LEDs, or the corrective action of increasing the total number of powered LEDs in the phototherapy device, or a combination of the corrective actions must be taken as the encapsulation material degrades. The wavelength of the UVA does not change significantly over the life of a UVA LED.

When used in 5 to 20 minute power cycles common in some phototherapy chambers, fluorescent light bulbs begin to noticeably degrade within 100 hours of use and have a total lifetime on the order of 1000 hours or less, and are very often replaced after 400 total hours of operation creating significant maintenance expenses. Therefore, there is a greatly reduced amount of maintenance required with the LED based phototherapy systems as opposed to fluorescent bulb phototherapy systems. The UVA LED has a consistent wavelength over the life of the LED, whereas the wavelength varies for fluorescent bulbs over the life of the fluorescent bulb. The average wavelength of the fluorescent bulb in the UVA range decreases and drifts into the UVB range which may result in a negative effect over the life of the fluorescent bulb, depending upon the particular phototherapy. Mercury vapor lamps without phosphors tend to suffer from drawbacks similar to those of fluorescent bulbs, where UVA and/or UVB output from the mercury vapor lamps may decrease over their lifetimes. Independent of UVA LED mounting method, whether encapsulated in UV sensitive material (epoxy resin) or encapsulated in UV insensitive materials (metal or plastic housing with quartz lens), the UVA LEDs have a longer useful life than fluorescent bulbs or mercury vapor lamps.

As previously stated, UVA LEDs may be used in combination with other UV producing light sources. LEDs incorporated into light therapy devices, including tanning, lupus therapy, teeth whitening therapy, hair regrowth therapy and psoriasis therapy devices, are not limited to the UVA type only. Other wavelengths LEDs are incorporated into the device in order to provide other types of light therapy. In addition to providing additional light therapy effects, other wavelength LEDs may provide visible light in an otherwise dark chamber.

In one embodiment, the LED device is contained in a tube, such as an acrylic tube, in the form factor of an industry standard fluorescent bulb with an internal power converter, an optional internal cooling system, and an optional temperature sensor. In yet another embodiment, the form is equipped with an internal light output feedback sensor to control the power to the cooling system or other fan. Alternatively, an external LED compatible power supply in the form factor for a high voltage fluorescent bulb ballast power supply can be used with the LED device in the fluorescent bulb form factor with house-power volt connector. This form factor allows for direct replacement of industry standard fluorescent power ballast when the industry standard fluorescent bulbs are replaced with LED fluorescent bulb form factors which do not contain internal power converters. The invention, manufactured in a standard fluorescent form factor, allows direct replacement with minimal modification to bulb fixtures already deployed in tanning chambers.

An external LED compatible power supply used with a low voltage LED array can be connected to a house-power connector. A low voltage LED array does not need an active internal high voltage power converter and thus has a lower cooling requirement but can still have an optional fan and optional temperature sensor and temperature controller.

In one embodiment, the device is equipped with optional adjustable rotating electrical connectors, friction plate, and fastener, allowing for setting arbitrary direction of the LEDs and circuit board. The device can also be equipped with a porous end-cap that allows for ventilation, such as passive or active ventilation. The porous end cap permits air flow when used, for example, with a fan. The industry standard electrical connection is composed of metallic pins and insulators, commonly referred to as Bi-Pin, RD2 and lead wires.

Flexible electrical connectors are a preferred embodiment, employing coiled wire but could also be composed of a track and slider connector for maintaining electrical connection while allowing for rotation of the end-cap with respect to the circuit board. The rotating components allows for adjustable directional alignment of light without having to rotate the connector on the fixture. In this embodiment, the LED device can advantageously replace one or more fluorescent bulbs in a typical fluorescent bulb based tanning chamber.

The UVA LED based florescent UV bulb replacement apparatus can come in a number of embodiments. In one embodiment, it incorporates an external heat sink for cooling of the components. The built-in power supply conditions house-power or high voltage or high frequency power into power suitable for driving LED circuits. A typical UVA LED fluorescent replacement lamp is composed of thousands of low power UVA LEDs or hundreds of high power UVA LEDs arrayed on a single fluorescent form factor circuit board. Heat sinks can be integrated into the UVA LED fluorescent replacement lamp. Combinations of heat sinks and fans can be integrated into said present invention. The form factor of the UVA LED fluorescent replacement lamp is similar to that of the florescent bulbs they replace but are not necessarily identical. UVA LED replacement lamps in a fluorescent bulb form factor may replace multiple fluorescent bulbs with a single set of connectors. The UV LED replacement fluorescent bulb set apparatus with a single or multiple sets of rotating electrical connectors can also be used. Optional modular components can create an arbitrary length of fluorescent bulb replacement utilizing special sockets, linking them end to end. Provisions for two-way control signals to selectively control individual or sub-sets of LEDs within the LED array can be contained within the connectors. Alternatively, the power lines can be modulated with two way time or frequency multiplexed coded signals in such a manner as to provide signal information to and from an LED power controller in proximity to the LEDs for the purpose of selectively controlling power to individuals or sub-sets of the LEDs.

The form can contain an array of a plurality of LEDs on a circuit board. The circuit board and LED array can be on one, two or more sides. The board can be flat, curved, angled (such as an obtuse or acute angle with one or two sides of the angle presented with an array). In yet another embodiment, the circuit board LED array is on one or more sides of a multiple angled circuit board, such as an open or closed angled circuit board. Where the board is curved, the curve can be concave, convex, or curvilinear, open or closed (such as a cylinder) with an array presented on one or both sides. In yet another embodiment, the circuit board can be flat (or other configuration), but the LED leads bent to allow direction orientation of LED, distinct from the board. In yet another embodiment, the circuit board is flexible, permitting bending, folding and/or formation to a desired contour. In yet another embodiment, the circuit board and LED array on all points of a curved three-dimensional circuit board.

The invention can be formed in a foldable LED array with multiple flat circuit boards which can be moved relative to each other. This array can be opened and placed on a surface such as a desk or table and can be folded and stored when not in use. A UV opaque safety shroud with an optional door and proximity safety switch encompassing foldable LED array can also be used.

The array of LEDs and circuit board can be made using a chip on board manufacturing process whereby there is no plastic encapsulation for the LED but another form of hermetic sealed cap made of a material with better UV resistant and UV transmittance properties than industry standard LED encapsulation. Industry standard LED encapsulation is typically UV sensitive and reduces the useful life of a UV LED where the LED encapsulation material degrades under UV light conditions over time and thus has a lower UV transmittance over use. Portions of the hermetic seal cap (25) may be composed of glass or quartz or other UV transparent material. Bonding wire can be used to mount the LED chips onto the circuit board. Chip on board mounting increases the lifetime of the UVA LED device because of the elimination of UV degradable encapsulating material.

UVA LED package can be mounted on the surface of the circuit board. The UVA LED package can optionally contain a focused lens typically found in 5 millimeter and 3 millimeter footprints on a circuit board. The hermetically sealed TO-66 package with UVA LED in a metal package with a UV transparent glass or quartz lens on a circuit board can be used. A glass or quartz lens transparent to UVA is preferred over other UV immune UV transparent material including plastic that is not degraded by UVA light.

In yet another embodiment, various UVA LED fluorescent bulb replacement lamp building block units referred to as UVA blocks, with integrated power and controller and the integrated cooling mechanisms can be used. Cooling can be implemented with fans or heat exchangers or active cooling means or combinations of these components. Cooling can occur across or through the array. Building blocks may be square or round and may be stacked to build a complete tanning device, referred to as stacked block device.

FIG. 1 shows an electrical schematic diagram for powering the LEDs in the series connected LEDs (47) in the low voltage LED array (22) and metallic pins (10, 12) and external LED compatible power supply (20) responding to control from optional external light output feedback sensor (174) and house power connector (36). This embodiment utilizes a resistor (46) to limit the current to the series connected LEDs (47). The series connected LEDs (47) have multiple LEDs or a single LED depending on the voltage supplied and number LEDs per controlled power lines (49). If the design goals of further embodiments of the present invention requires a controllable power line for each LED then a single LED in the series connected LEDs (47) and LED (5) are identical. There is a tradeoff between providing control to each LED and the cost associated with the control circuits. Additionally, there is a tradeoff between cost of power supply and the failure of a single LED in an open failure mode to block the delivery of current to multiple LEDs in the series connected LEDs (47). LED compatible power supplies (20) designed for supplying current to individual LEDs is more expensive because the voltage conversion is wider and the current output is higher. The total current output from LED compatible power supply

(20) is reduced by a factor calculated as the number of power lines (49) divided by the total number of LEDs in the further embodiment of invention (22). Therefore, depending upon the application and allowable failure modes, LEDs may have an arbitrary number of LEDs in series depending on the trade-off and application requirements. Also shown is a variable power supply which charges capacitors (45) in a selective manner.

Figure 2:
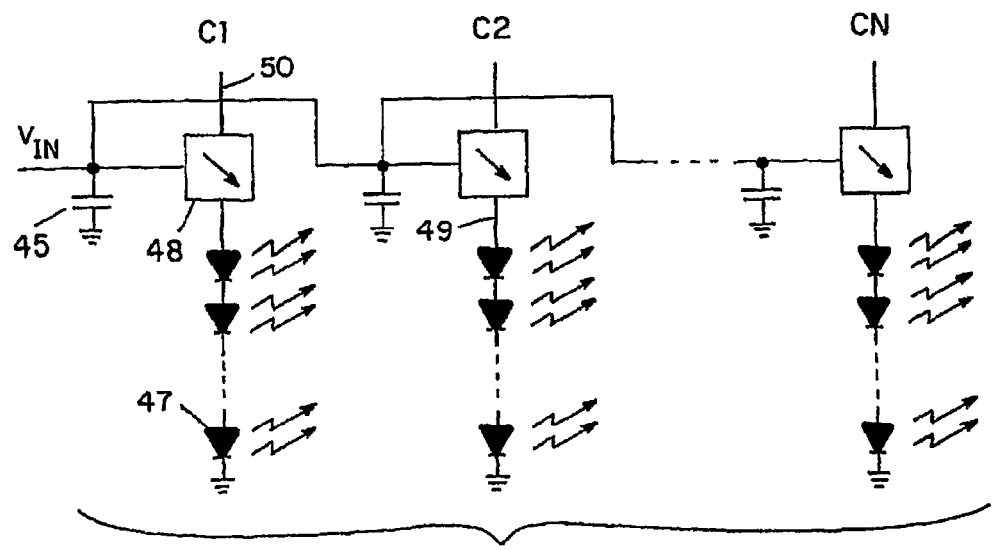
FIG. 2 shows an electrical schematic diagram of a LED power control circuit.

FIG. 2 shows an electrical schematic diagram of a LED power control circuit that utilizes a current control (48), and an optional capacitor (45). Current control (48) supplies current series connected LEDs (47) via controlled power line (49) power control line (50). Current control (48) may optionally vary the current delivered to series connected LEDs (47) over time as the encapsulation UV transmittance varies. Current control (48) may optionally vary the current delivered to series connected LEDs (47) over time to provide specific tanning patterns according to achieving arbitrary light therapy specific results.

Figure 3:
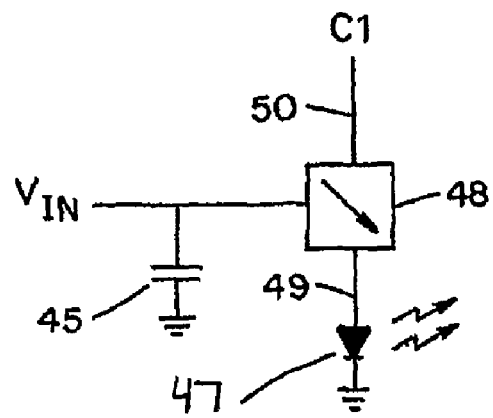
FIG. 3 shows an electrical schematic diagram of a LED power control circuit.

FIG. 3 shows an electrical schematic diagram of a LED power control circuit that utilizes a current control (48), and a capacitor (45), where current control (48) is attached to a single LED (5) connected to controlled power line (49) power control line (50).

Figure 4:
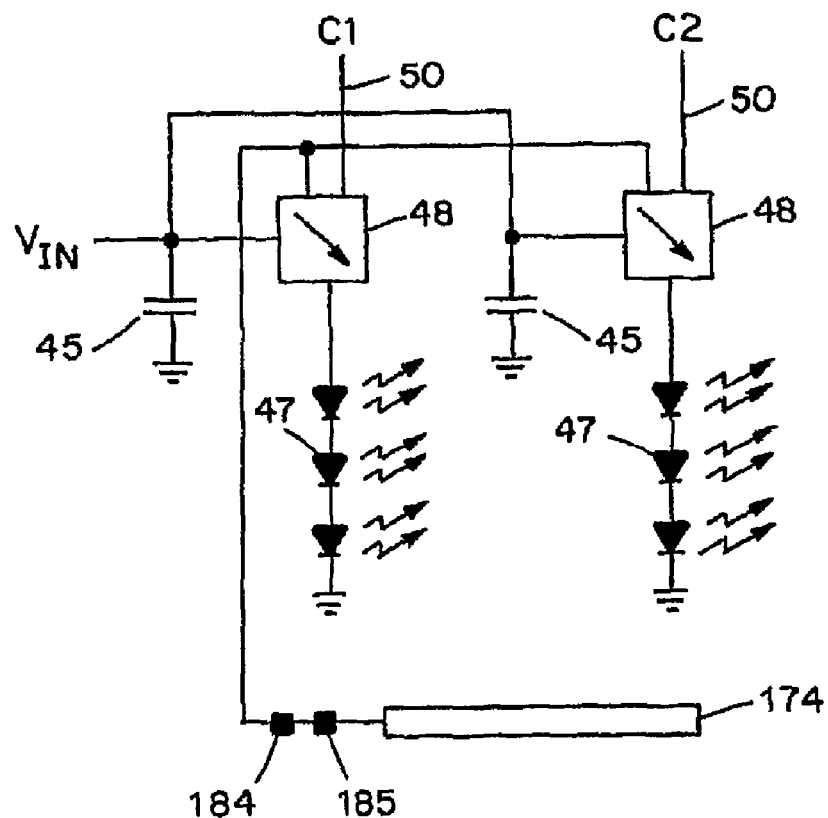
FIG. 4 shows an electrical schematic diagram of a LED power control circuit Also shown are permanently mounted connector and portable connector which allows said external light output feedback sensor to be moved around within the tanning chamber and removed from the tanning chamber.

FIG. 4 shows an electrical schematic diagram of a LED power control circuit that utilizes said current controls (48), and an optional said capacitors (45). Said current controls (48) supplies current to said series connected LEDs (47) via said controlled power lines (49) responsive to said power control lines (50) and said external light output feedback sensor (174). The method of calibrating each separate said current controls by selectively turning on one said current control at a given time in order to measure the light output from the said series connected LEDs and calibrate each set of said series connected LEDs (47) separately. Current control (48) may optionally vary the current delivered to series connected LEDs (47) over time as the encapsulation UV transmittance varies. Also shown are optional permanently mounted connector (184) and portable connector (185) which allows said external light output feedback sensor (174) to be moved around within the phototherapy chamber and removed from the tanning chamber. The light output sensor may also be fixed inside the chamber or mounted to a translating and rotating mechanism to scan the chamber in a mechanical and automated manner.

The use of multiple LEDs of various wavelength within a tanning chamber can also be used. Specifically useful for tanning are near-UV-blue LED, blue LED, blue-green LED, multi-bright LED, solid state laser light emitting device that radiates light capable of tanning or capable of providing light therapy of some benefit. Also envisioned is solid state nanostructure UV-laser chip for use in controlled multi-directional area specific tanning device optionally associated with camera for feed-forward control for determining exposure avoidance area and feedback control of specific light exposure areas. Alternatively, one may use tanning area specific mechanical translation device with laser chip based focused light source. Another embodiment includes focused light source utilizing LEDs on circuit board and translucent lens, optional translucent lens, and translucent lens to create a tightly focused light source which can be selectively powered depending on specific areas of skin to expose to light and in particular UVA light. Another embodiment includes focused light source utilizing any light source lens and translucent lens, optional UV translucent lens, and UV translucent lens to create a tightly focused UVA light source which can be selectively controlled by light controller depending on specific areas of skin to expose to light and in particular UVA light. Light controller may be a blocking type shutter or a deflecting mirror to effectively modulate the light emitting from focused light source.

In yet another embodiment, the wavelength of the LED can be controlled. For a given junction electric current and junction temperature, UVA LEDs generally emit photons around a peak wavelength in a narrow (e.g., approximately 5 nm or 10 nm) bell curve range of wavelengths. These curves may typically be characterized by a full width half maximum (FWHM) of about 3 nm to 20 nm. Differing LED types have differing peak wavelengths. UVA LEDs allow fine control for generating wavelengths. That is, the use of a plurality of the same or distinct LEDs can be used, optionally, in combination with multiple distinct operating conditions to independently control the emitted wavelengths. For example, a set of LEDs of a single LED type can be controlled with different junction currents and power duty cycles among the individual LEDs within the set of LEDs of a single LED type in order to broaden the spectral density of UV wavelengths emitted by the set as a whole. In addition, multiple sets of LEDs of differing types can be used to broaden the spectral density of UV wavelengths to a greater extent than is possible with a set of LEDs of a single type. The purpose of the manipulation of the LEDs is to be able to tailor the UV wavelength for a specific individual tanning session or specific light therapy requirements.

LEDs as a UV light source provide the capability of controlling the wavelengths produced. LEDs of varying types produce light at various wavelengths. By selectively controlling specific LED types within the light therapy device sequences of light can be applied at predetermined or arbitrary patterns with varying wavelengths. Examples of commercially available LED types include, but are not limited to, Cree (peak wavelengths of 405, 395 and 365 nm), Nichia (peak wavelengths of 395, 380, 375 and 365 nm), Toyoda Gosei, Marubeni America Corporation (364-380 nm), Crystal IS in collaboration with Palo Alto Research Center (355-365 nm). Additional LEDs that can be used in this device include organic light emitting devices.

Another method for controlling wavelength is based on varying the electrical current and/or junction temperature to the LEDs.

A single LED type at a given current and temperature will generally produce photons that have a wavelength distribution resembling a bell curve. Therefore, controlled current pulsing in combination of varying the duty-cycle of the LEDs power will control current and temperature conditions of the LED and results in wavelength shifts that will have additional light therapy benefits.

Generally, for a given UVA LED type, the shorter wavelengths, within the band of producible wavelengths, results from the lower junction currents.

An additional means to control the peak wavelength is varying the LED ambient cooling mechanism (e.g. fans, thermoelectric cooler, peltier effect cooling device, and compressor based air conditioners). A UVA LED assembly control system, comprising an analog or digital computer, a suitable algorithm, wavelength sensors, light intensity sensors, skin proximity sensors, and user interface for programming desired results, can be used to calculate the required variations to the current controllers and the duty cycle controllers and the ambient temperature controllers in order to produce a specific peak wavelength from a given set of UVA LEDs. The time of exposure for any given light therapy application may vary depending on the wavelength required and can be determined a-priori or in real time through such a control system.

LED type detecting sensors can be used to detect the types of LED that are present within the chamber. The use of such sensors may reduce the hazard of programming the control system for the wrong set of UV LED types. The detector can be mechanical in action with specific LED assemblies having specific cutouts for indicating type. The detector can be an RF ID system or other non-mechanical identification system. The detector can send various standardized controlled signals and power to the LED array to determine the capabilities of the LED assembly for use in the programming the control system.

Non-conducting housing for electrical connectors connecting power and control circuits between multiple modular LED replacement fluorescent bulb components and rotating power connectors can be used. External light output feedback sensor can be used to increase safety.

Nanostructure UV Light Emitting Device

Figure 5A:
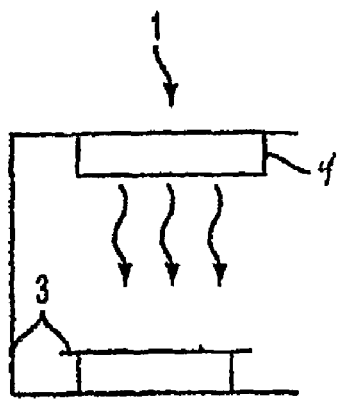
FIGS. 5A and 5B are schematic side views of systems according to embodiments of the present invention.
Figure 5B:
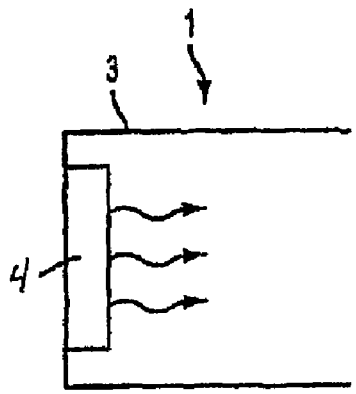

In a second aspect of the invention, the present inventor has realized that a system for a phototherapy, including skin tanning, lupus therapy, teeth whitening, hair regrowth and psoriasis may use a nanostructure UV light emitting device. This allows a control of the spectral distribution (including single or multiple peak wavelengths) of the UV light as well as provides UV light with a narrow wavelength distribution (i.e., a narrow peak width) or a broad wavelength distribution (i.e., a broad peak width). The choice of a narrow or broad wavelength distribution will depend, at least in part, on the intended application. FIGS. 5A and 5B illustrate the system (1) which contains a chamber (3) adapted for at least one of these phototherapies and the nanostructure UV light emitting device (4). The system (1) may be used solely for a single phototherapy or a combination of phototherapies depending on the need of the person being subjected to the UV light. FIG. 5A illustrates a phototherapy system for the prone body position, which is commonly referred to as a tanning or a phototherapy bed. FIG. 5B illustrates a phototherapy system for upright body positions, which is commonly referred to as a tanning or a phototherapy booth.

The nanostructure UV light emitting device comprises at least one of a nanoparticle and a nanowire UV light emitting device. In some embodiments, the UV light emitting device emits only UVA light. In other embodiments the UV light emitting device also emits visible and/or infrared radiation in combination with UV light. These latter embodiments may be advantageous where the light emitting devices are intended for general purpose lighting or in phototherapies for the treatment of conditions that respond to visible and infrared radiation.

The term UV light includes radiation having a peak wavelength between 160 and about 400 nm rather than visible light having a wavelength between above about 400 and below about 700 nm. UVA light has a peak wavelength between about 290 and about 400 nm. The nanoparticles and nanowires emit light (i.e., radiation) with a very narrow peak width due to their size rather than due to their chemical composition. Thus, in contrast to conventional ceramic phosphors which emit light with a broad peak width due to their chemical composition and activator ion content, nanoparticles and nanowires emit light with varying peak wavelength due to varying their size (i.e., diameter or thickness). Furthermore, some materials, such as silicon, which ordinarily do not emit light in bulk form, emit light in nanoparticle form due to the nanoparticle size. Thus, the nanoparticle or nanowire size may be selected such that the nanoparticles or nanowires emit only UVA light, but no UVB light. Furthermore, nanoparticle or nanowire size may be selected such that the nanoparticles or nanowires emit only UVA-1, UVA-2 and/or UVA-3 light depending on the desired effect, since the peak width of the emitted UV light is narrow.

Nanoparticles may be any suitable nanoparticles, such as nanocrystals or quantum dots, having a diameter less than 100 nm, such as a diameter of 2-20 nm, for example. For example, metal, semiconductor, as well as metal or semiconductor oxide and/or nitride nanoparticles may be used. Semiconductor nanoparticles include materials from Groups IV (Si, Ge, SiC, SiGe), II-VI (CdS, ZnS, CdSe, ZnSe, ZnTe, CdTe), IV-VI (PbS, PbSe, PbTe) or III-V (GaAs, GaP, GaN, InP, InAs). Ternary and quaternary semiconductor nanoparticles, such as CdZnS, CdZnSe, CdZnTe, CdZnTeSe, CdZnSSe, GaAlAs, GaAlP, GaAlN, GaInN, GaAlAsP and GaAlInN for example, may also be used. Ceramic or metal oxide nanoparticles may also be used, such as silica, alumina, titania, zirconia, yttria stabilized zirconia, yttria, ceria, spinel (for example, $MgO*Al_2O_3$) and tantalum pentoxide, as well as other suitable ceramics having a more complex structure, such as radiation emitting phosphors (for example, YAG:Ce ($Y_3Al_5O_{12}$:Ce) and various halophosphate, phosphate, silicate, aluminate, borate and tungstate phosphors) and scintillators (for example, LSO, BGO, YSO, etc.). Other metal oxide nanoparticles, such as zinc oxide, indium oxide or indium tin oxide or metal nitride nanoparticles, such as aluminum nitride may also be used. Metal nanoparticles may be pure metal or metal alloy nanoparticles, such as Al, Fe, Cu, Ni, Au, Ag, Pt, Pd, Ti, V, Ta, W, Mn, Zn, Mo, Ru, Pb, Zr, etc. and alloys thereof.

Other materials, such as Boron Carbide, Titanium Oxide (TiO), Silicon Carbide (SiC), Antimony (Sb), Arsenic (As), Bismuth (Bi), Cadmium (Cd), Carbon (C), Gallium (Ga), Germanium (Ge), Indium (In), Phosphorus (P), Selenium (Se), Sulfur (S), Tellurium (Te), Calcium (Ca), Chromium (Cr), Cobalt (Co), Magnesium (Mg), Tantalum (Ta), Silicon Arsenide Germanium Telluride (SiAsGeTe), Vanadium Oxide, Zinc Germanium Phosphide (ZnGeP2), Zinc Germanium Phosphide (ZnGeP), Aluminum Antimonide (AlSb), Aluminum Arsenide (AlAs), Aluminum Phosphide (AlP), Gallium Selenide (GaSe), Gallium Telluride (GaTe), Indium Antimonide (InSb) and Silicon Arsenide Telluride (SiAsTe) may also be used.

Nanoparticles may be provided in the UV light emitting device (4) in any suitable form. For example, the nanoparticles may be located as a solid layer or layers on a UV transparent and UV resistant material substrate. The solid layer may also contain a UV transparent and UV resistant binder or filler if desired. Alternatively, the nanoparticles may be located in a suspension. The fluid of the suspension may comprise any suitable UV transparent fluid. Preferably, the fluid comprises a fluorocarbon fluid, such as perfluorocarbon, chlorofluorocarbon or hydrofluorocarbon fluid. For example, the fluid may comprise 1,1,1,2 tetrafluoroethane also known as R134A or perfluorocarbon fluids sold under the PPx series from F2 Chemicals Ltd. in Lea Town, U.K., such as the PP6 perfluorocarbon fluid. The R134A fluid is provided under elevated pressure to remain in the liquid state at room temperature. Other fluids which are liquid at atmospheric pressure at room temperature may also be used. If the nanoparticles are located in a suspension, then the suspension is located in a sealed vessel or tube made of a UV transparent and UV resistant material. If desired, the device (4) may also contain a pump or vibrator which maintains the suspension under turbulent flow to prevent the nanoparticles from settling on the surface of the vessel.

Nanowires may be any suitable nanowires having a thickness (i.e., diameter) of less than 150 nm, such as a thickness of 70-100 nm, for example. The nanowires may comprise any suitable material, such as metal oxide material. For example, zinc oxide, indium oxide and indium tin oxide nanowires may be used. Any suitable length of nanowires may be used.

The system (1) further preferably comprises a UV excitation source (7). The source (7) is positioned to provide UV excitation radiation of a first peak wavelength onto the nanostructure UV light emitting device (4) to cause the nanostructure UV light emitting device to emit UVA light having a second UVA peak wavelength longer than the first peak wavelength. Any suitable UV excitation source may be used.

Figure 6:
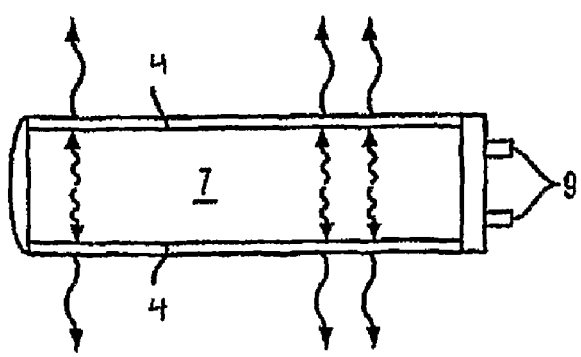
FIGS. 6, 7, 8A, 8B, 9 and 10 are cross sectional side views of nanostructure UV light emitting devices according to embodiments of the present invention.

In one preferred embodiment shown in FIG. 6, the UV excitation source (7) comprises a gas vessel comprising a gas which is adapted to emit the UV excitation radiation in response to a stimulus. For example, the source may be a gas lamp tube filled with a gas such as Ar or Hg which emits UV radiation when a voltage is applied to the electrodes (9) of the gas tube. The UV light emitting device (4) in this embodiment comprises at least one layer of nanoparticles coated on an inner surface of at least one UV light transparent wall of the gas vessel or tube (7). In other words, the conventional phosphor in a fluorescent lamp (7) is replaced with or combined with one or more layers of nanoparticles which emit UVA light in response to UV excitation radiation emitted by the gas. In this case, rather than using an expensive UV emitting lamp, a cheap germicidal or white light emitting lamp may be used instead, but with replacing the white light emitting phosphor with UVA light emitting nanoparticles. Preferably plural layers of nanoparticles are coated on the inner surface of the gas tube or vessel (7) to prevent the UVB or UVC radiation emitted by the gas, such as 254 nm UVC radiation, from being incident on the skin of a person in the phototherapy chamber (3). The UV exciting radiation from the gas in vessel (7) is incident on the nanoparticles (4), which emit UVA light in response to the incident radiation. The nanoparticles (4) block the UV excitation radiation, such as UVC radiation, from exiting the vessel or tube (7). Alternatively, another UV emitting LED could be used as an excitation source.

Figure 7:
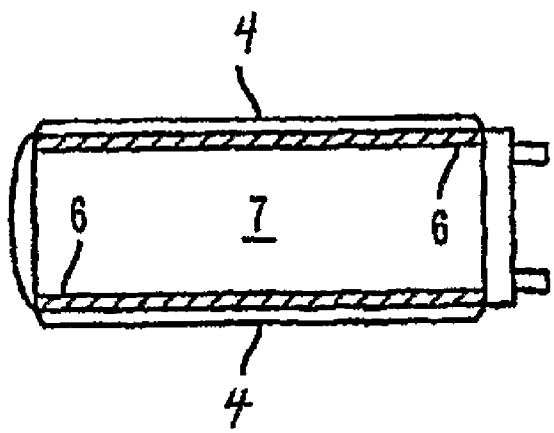

In another preferred embodiment shown in FIG. 7, the UV excitation source (7) comprises any suitable UV lamp which optionally contains a UV emitting phosphor (6) on its inner walls. The UV light emitting device (4) comprises at least one layer of nanoparticles coated on an outer surface of the UV lamp (7). The UV exciting radiation from the lamp from the lamp (7) is incident on the nanoparticles (4), which emit UVA light in response to the incident radiation.

Various other UV excitation sources (7) may be used. For example, the UV excitation source may comprise a focusing lens which focuses solar radiation onto the UV light emitting device. Furthermore, while an optical UV excitation source (7) is preferred, in an alternative aspect of the invention, an electrical excitation source may be used instead. In this case, the nanoparticles or nanowires (4) are located between two electrodes. At least one electrode is preferably made of an electrically conductive and UV transparent material, such as indium oxide, tin oxide or indium tin oxide (ITO). When a voltage is applied between the electrodes, the voltage causes the nanoparticles or nanowires to emit UV light.

It should be noted that the nanoparticles or nanowires (4) do not have to be placed directly on the UV excitation source (7). The nanoparticles or nanowires may be located on a separate substrate, such as a UV transparent substrate, or in a separate suspension in a vessel, which is located between the UV excitation radiation source (7) and the portion of the chamber (3) which houses the person undergoing phototherapy.

Figure 8A:
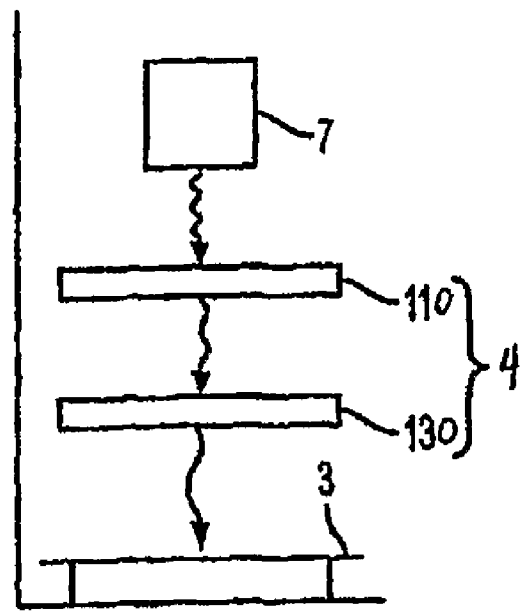

In a third embodiment shown in FIG. 8A, the UV light emitting device (4) comprises a plurality of layers of nanoparticles or nanowires arranged in a direction extending from the UV excitation radiation source (7) to the portion of the chamber (3) which houses the person undergoing phototherapy. The nanoparticles or nanowires in each layer emit radiation having a different peak wavelength from the nanoparticles or nanowires in other layers. Preferably, the peak wavelength of the UV radiation emitted by the nanoparticles or nanowires increases in each subsequent layer in the direction from the UV excitation source (7) to the portion of the chamber (3) which houses the person undergoing phototherapy. In other words, the nanoparticles or nanowires in each layer located closer to the person's skin (i.e., farther from the UV excitation source (7)) emit radiation of a longer wavelength that those in another layer located farther from the person's skin (i.e., closer to the UV excitation source (7)). This allows the stacked layers of nanoparticles or nanowires to gradually or stepwise upconvert the UVB and/or UVC radiation emitted by the UV excitation radiation source (7) to desired UVA radiation. There may be two or more layers of nanoparticles or nanowires.

For example, as shown in FIG. 8A, the UV excitation radiation source (7) may emit 254 nm peak UVC radiation. A first layer (110) of first nanoparticles or nanowires is located proximal to the UV excitation source (7). The first nanoparticles or nanowires emit UV light of a third peak wavelength, such as 315-340 nm, which is longer than the 254 nm peak wavelength, when irradiated with the UV excitation radiation from source (7). A second layer (130) of second nanoparticles or nanowires is located distal from the UV excitation source, such that the first layer (110) is located between the second layer (130) and the UV excitation source (7). The second nanoparticles or nanowires emit UV light of the second peak wavelength longer than the third peak wavelength when irradiated with the UV light from the nanoparticles or nanowires of the first layer (110). For example, the nanoparticles or nanowires of the second layer (130) may emit UVA-1 radiation having a peak wavelength of 345-355 nm or 395-405 nm when irradiated with UVA-2 or UVA-3 radiation from the first layer (110). Additional layers of nanoparticles or nanowires may be located between layers (110) and (130) to make the radiation wavelength upconversion (i.e., energy down conversion) even more gradual.

Layers (110), (130) may be formed directly on each other with the UV excitation source (7) acting as a substrate. Alternatively, each layer (110), (130) may be spaced apart from the adjacent layer and each layer may be formed on a separate UV transparent substrate, such as glass, plastic or quartz substrate, or in a separate solution holding vessel.

Figure 8B:
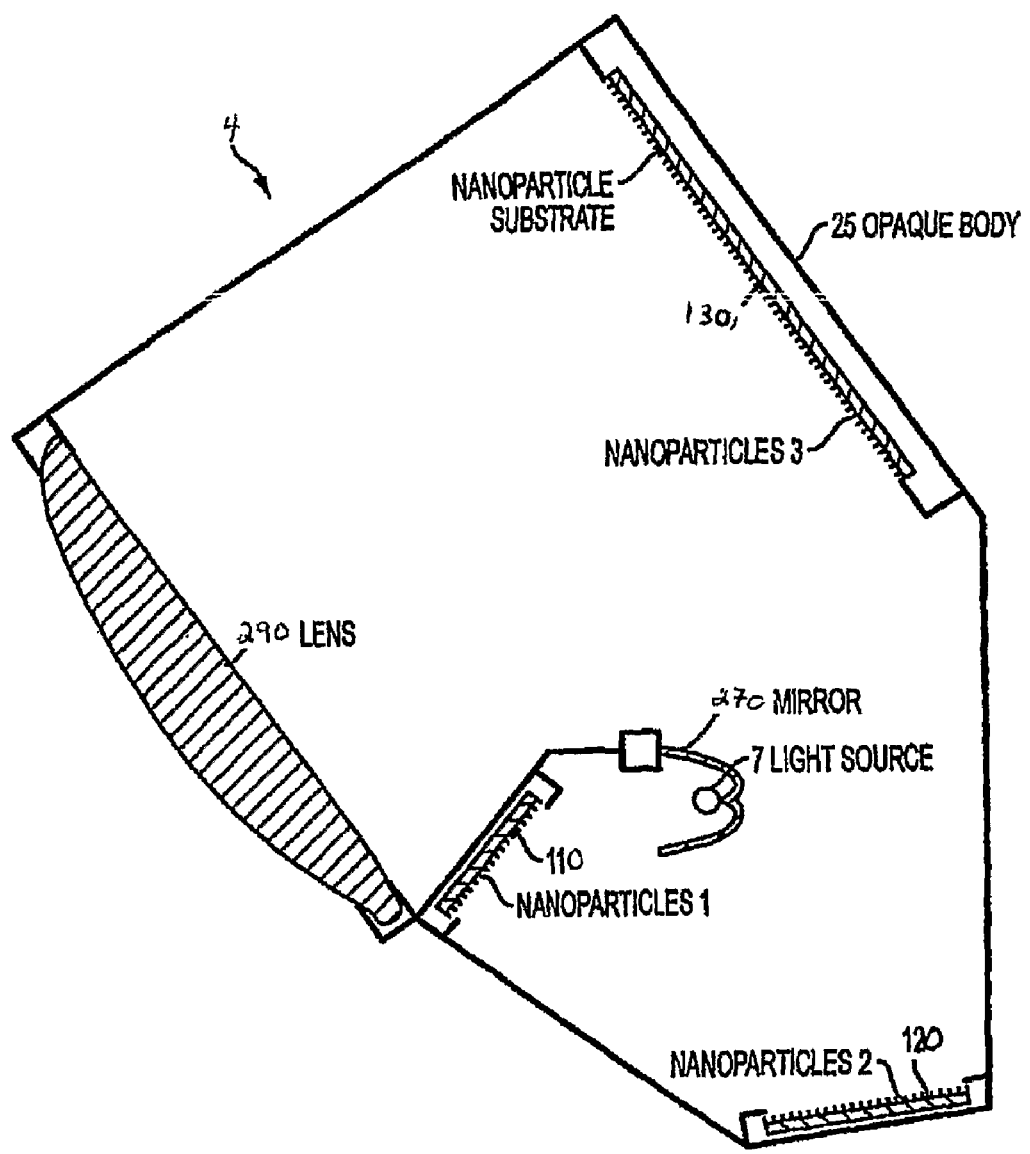

FIG. 8B illustrates an alternative aspect of the third embodiment. In this aspect, three layers of nanoparticles or nanowires (110), (120) and (130) are arranged in a clam-shell type housing (250) comprising an opaque body. The UV excitation source (7) is located in the interior portion of the housing (250). A mirror (270) shields the back side of the source (7). The first layer (110) of nanoparticles or nanowires is located opposite to the source (7) and mirror (270), such that UV excitation radiation from source (7) and mirror (270) is incident on the first layer (110). The second layer (120) of nanoparticles or nanowires emits UV light having a peak wavelength between those of the first (110) and third (130) layers. The second layer (120) is positioned in the housing to receive UV light from the first layer (110) and to emit UV light of a longer wavelength onto the third layer (130). The third layer (130) is positioned to receive UV light from the second layer (120) and to emit UV light of an even longer wavelength out of the housing through a lens (290) and through an optional long wavelength filter, which blocks shorter wavelength UV light from the source (7), first layer (110) and second layer (120) from exiting the housing (250). If desired, a light absorbing surface may be located behind the layers (110), (120) and (130). It should be noted that the term "layer" as used herein includes a nanoparticle or nanowire solid layer as well as a nanoparticle suspension located in a vessel. By using the clam-shell shaped housing (250), UV light of one or more desired wavelengths from layers (110), (120) and/or (130) exits the housing (250). In should also be noted, that although this clam-shell design for a nanoparticle-based light source is described primarily in conjunction with various phototherapies, this device may also be employed for general purpose lighting.

Figure 9:
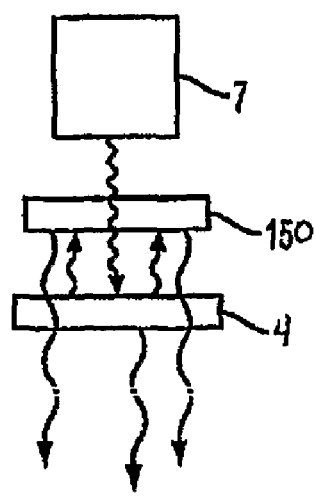

In a fourth embodiment of the present invention shown in FIG. 9, an optical filter (150) is located between the UV excitation source (7) and the UV light emitting device (4). The filter (150) is transparent to the shorter wavelength UV excitation radiation from source (7). However, the filter (150) reflects UV light of a longer peak wavelength emitted by the UV light emitting device (4). The filter (150) may be a holographic filter or any other suitable filter having the above described property. This configuration is advantageous when nanoparticles are used as the light emitting device (4). The nanoparticles emit UV light in all directions. However, the filter (150) reflects UV light emitted toward the source (7) back in the direction of the portion of the chamber (3) in which the person is to be located.

Figure 10:
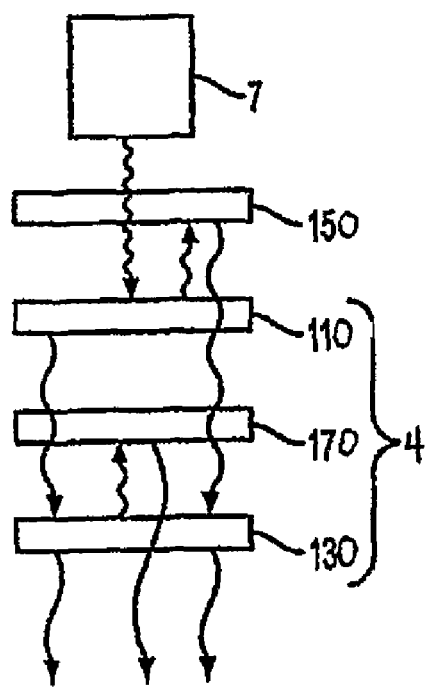

The fifth embodiment is a combination of the third and fourth embodiments. As shown in FIG. 10, the UV light emitting device (4) comprises a plurality of layers (110), (130) of nanoparticles or nanowires arranged in a direction extending from the UV excitation radiation source (7) to the portion of the chamber (3) which houses the person undergoing phototherapy. The nanoparticles or nanowires in each layer (110), (130) emit radiation having a different peak wavelength from the nanoparticles or nanowires in other layers. The peak wavelength of the UV radiation emitted by the nanoparticles or nanowires increases in each subsequent layer in the direction from the excitation radiation source (7) to the portion of the chamber (3) which houses the person undergoing phototherapy. A filter (170) is located between adjacent layers of nanoparticles or nanowires. The filter (170) is transparent to the shorter wavelength UV light from the layer (110) proximal to the UV excitation source (7). However, the filter (170) reflects UV light of a longer peak wavelength emitted by layer (130) distal from the UV excitation source (7). If the device (4) contains more than three layers of nanoparticles or nanowires, then a different filter may be located between each pairs of layers.

Figure 11:
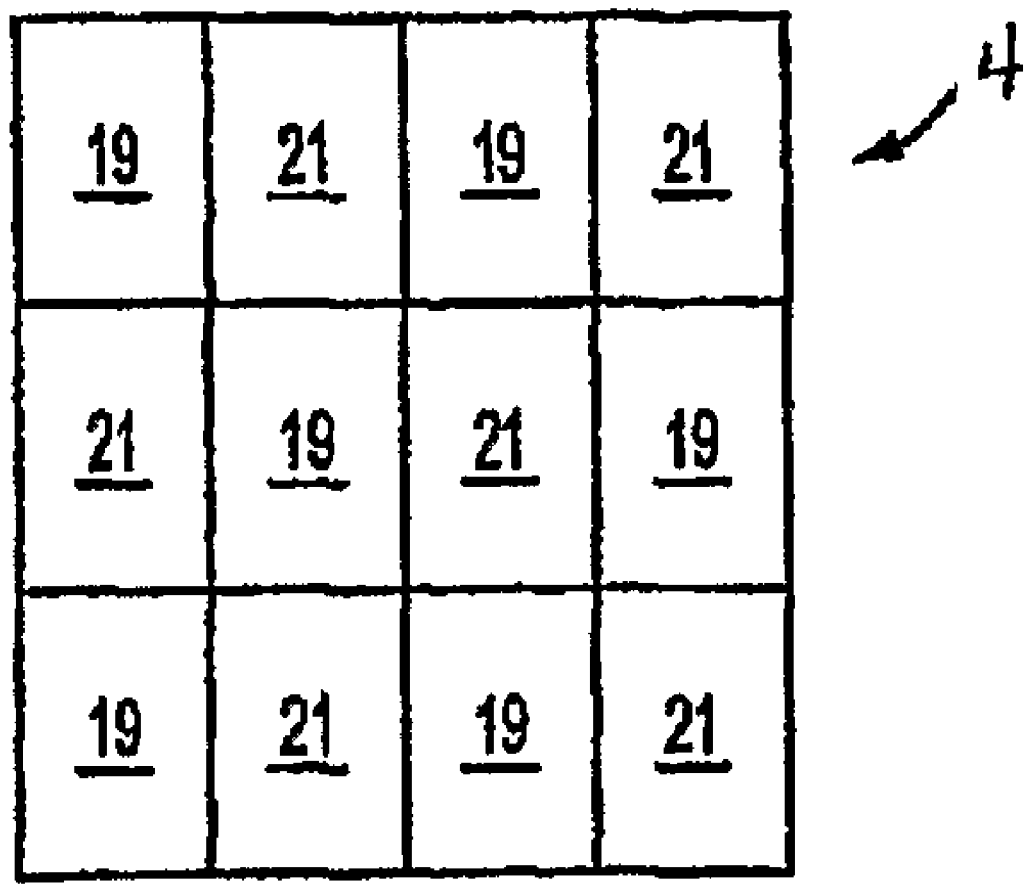
FIG. 11 is a bottom view of a nanostructure UV light emitting device according to an embodiment of the present invention.

In a sixth embodiment, the nanoparticles or nanowires are arranged in pixels as shown in FIG. 11. The nanoparticles or nanowires in each pixel can be separately activated by a dedicated UV excitation radiation source or by dedicated electrodes to selectively tan or treat a desired portion of skin on the person undergoing phototherapy. In one aspect of the sixth embodiment, the UV light emitting device (4) includes a first set of pixels (190) of first nanoparticles or nanowires. The first nanoparticles or nanowires are adapted to emit UV light having a predetermined first peak wavelength. The device (4) also includes a second set of pixels (210) of second nanoparticles or nanowires. The second nanoparticles or nanowires emit UV light of the second peak wavelength longer than the first peak wavelength. If desired, additional sets of pixels may be provided. Pixels of the first set of pixels (190) are interspersed with pixels of the second set of pixels (210).

All pixels may be turned on at once to provide UV light having a plurality of different peak wavelengths or one set of pixels may be selectively activated while the other sets remain turned off. In this case, the peak wavelength of the UV light may be selectively tailored for each individual based on the desired darkness of the tan, the individual's skin color or a selection of a particular wavelengths to treat a particular condition during phototherapy.

In a seventh embodiment, the system (1) contains the UV light emitting device (4) with exchangeable nanoparticles or nanowires to vary the peak emission wavelength of the device (4). For example, if the nanoparticles are located in a suspension in a sealed vessel, then the vessel may be opened and the suspension replaced by another suspension having nanoparticles which emit light of a different wavelength from the nanoparticles in the original suspension. Preferably, the vessel comprises non-stick surfaces to prevent nanoparticle adhesion. Alternatively, the entire vessel housing the suspension may be removed from the system and replaced with another vessel containing a different suspension of different nanoparticles which emit light of a different peak wavelength than the nanoparticles of the original suspension. If the nanoparticles or nanowires are coated as a solid layer on a substrate or substrates, then the substrate or substrate may be easily removable from the system to allow the system operator to insert a substrate or substrates containing nanoparticles or nanowires which emit light of a desired peak wavelength into the system (1).

A method of operating the system (1) for phototherapy, including skin tanning, lupus therapy, teeth whitening, hair regrowth or psoriasis therapies, includes providing UVA light from a nanostructure UV light emitting device (4) onto a skin of a human subject who is located in a chamber (3) adapted for at least one of these phototherapies in order to provide phototherapy for the skin.

The method also includes providing UV excitation radiation of a first peak wavelength from a UV excitation source (7) to the UV light emitting device (4). The method also includes emitting the UVA light having a second UVA peak wavelength longer than the first peak wavelength from the UV light emitting device (4) in response to the provided UV excitation radiation.

In an eighth embodiment, blue light having a wavelength of about 400 to about 415 nm, such as about 405 nm is used instead of UV light. Light of this wavelength is sometimes called violet or purple rather than blue. Any suitable blue or violet light emitting device (4) which emits light of this wavelength may be used, including a lamp, a light emitting diode, nanoparticle or nanowire containing device (4). The light emitting diode, nanoparticles and nanowires are preferred because they have a narrower emission peak width. For light emitting diodes, blue light emitting diodes based on GaN, SiC or ZnSe semiconductor materials may be used. Tanning with light in the 400-415 nm wavelength range may provide a longer lasting tan than tanning with UV light. Preferably but not necessarily, the light emitting device emits light having substantially no wavelengths outside the about 400 nm to the about 415 nm range, such as emitting less than 1% of light having wavelengths outside the about 400 nm to the about 415 nm range. The device (4) of this embodiment may be used in combination with the configuration(s) of the other embodiments described herein.

Illustrative Device Designs

Both the UV LED-based systems, devices and chambers and the nanostructure-based systems, devices and chambers may include a variety of components and may have a variety of geometries and designs, based on the particular therapy being delivered. By way of non-limiting examples, embodiments of systems, devices and chambers for both types of UV sources (i.e., for both the UV LED-based systems and the nanostructure-based systems) are provided here.

In these systems, devices and chambers, various wavelength LEDs or nanostructure UV light emitting devices can be used separately or in combination and may be selected and controlled for use in phototherapies and as multi-wavelength light bulbs for general purpose lighting. The LEDs and/or nanostructure UV light emitting devices may be used in combination with other light sources that emit in the UV, visible (VIS) or infrared (IR) to provide a desired radiation spectrum. In one example, the LEDs and/or nanostructure UV light emitting devices may be combined with one or more conventional light bulbs in a single system. In other examples, UVA can be used in combination with yellow, orange, green, blue, red, violet, IR, fluorescent, and/or UVC, as modular or fixed designs, in combination or separate. Bulbs capable of producing various wavelengths can be combined in arbitrary patterns to produce arbitrary light therapy devices. Further, the wavelength produced by any one UV source can be varied.

The chambers incorporating the UV sources can be a booth or bed and can be enclosed or open. The chamber can be composed of a variety of materials including UV opaque film or UV opaque solid walls to control the exposure direction of the light. The UV sources (i.e., LEDs or nanostructure devices) can be directed to expose light within the chamber and can be on the same or on independent controls. In general, the internal surface of the chamber walls will be UV reflective while the external surface and the wall itself will be UV opaque.

For example, height dependent chambers with light saving feature sections of controllable UV sources can selectively be turned off where the person in the phototherapy chamber does not require all of the controllable light sources (including UVA LEDs and UVA nanostructure emitters) turned on because of height, or because of the desire to treat (or not treat) specific parts of the body. For example, the light sources can be arranged and selectively powered to avoid treatment of pre-cancer sites or moles. A UV source controller may be present in the chamber (or outside the chamber) to adjust the height, pattern, brightness and other features of the phototherapy system. The controller has a manual controller input, an automatic height sensor input, or both. The controller can adjust brightness and duration of exposure based on the temperature of the devices with optional temperature sensor input. The controller can vary the pattern accordingly and indicate to the user the best direction to stand and in what position the extremities should be in order to have the best solution for obtaining the desired results if, for example, the chamber does not have a full 360 degrees of phototherapy. Alternatively, the height controller may be an external component to facilitate a full 360 degree of controllable UV source array. Additionally, one may include a master controller and master-slave communication device and slave-slave communication device.

A person in the upright or a person in the prone position can be exposed to a directionally controllable focused light source controlled either by controllable mirrors or controlled by phototherapy area specific mechanical translation device of focused light source or controlled by a combination of both methods to effectively treat only the desired areas. This allows blemished problem skin or pre-cancerous skin problem to remain unexposed to the focus light.

A history of the use of the phototherapy systems can be stored and later accessed in order to improve the effectiveness of the control system. Historical information can include one or more of the following: number of sessions, session type, duty cycles, electric current levels, power duty cycles, ambient temperatures, UV exposure patterns and other UV source type specific information. Information can also be stored in a remote location and a serialized coded key device (e.g. a memory chip, ROM, battery backed RAM, or optical memory) will provide the control system with a means of look-up for prior history of the phototherapy system. The history of use of a particular phototherapy system can be used in the control systems to calculate wavelength and exposure times for a desired light therapy session. This may prove to be a very desirable feature in light of the importance of keeping an accurate patient treatment records.

It is noted that personal slippers can improve health conditions on the surface of the device when shared, by reducing germ contamination between individuals. The personal slippers can be UV translucent or UV opaque depending on choice of person undergoing phototherapy.

Preferably, the person undergoing phototherapy can be equipped with radio identification, UV opaque protective eye-wear (with an optional safety feature to indicate that the eyewear is worn) and user interface. The user communication and safety control system can be accessible from the inside and/or outside of the chamber containing receiver for UV opaque protective eye-wear with an identification device used to indicate the presence of the UV opaque protective eye wear within the chamber. The identification device may be wireless or a wired communication device.

The form factors for incorporating the UV sources can be optionally contoured to fit or conform to the body or body part of the individual user. For example, the form may be a face tanning system incorporating LEDs or nanostructure-based emitters and circuit board. Such a face tanning system may in the form of a face mask (optionally extending to the neck area or below), with optional ports for the eyes, nose and/or mouth and can incorporate one or more optional fans at the edge(s) of the mask for ventilation and cooling purposes, optional audio speakers for listening to music or environmental sounds with either stereo or quadraphonic audio input and/or microphone for verbal communications with optional telephonic capabilities, microphone input for further communications capability. Additionally, the mask can be characterized by an external UV source compatible power supply with optional timer control, power switch, house power connector and/or external battery connector, an optional programming keypad for entering user codes and lockout features, key-lock, proximity switch to ensure a proper fit of the mask by controlling the closing of the mask and the operation of the hinge attached to UV opaque face shield. A circuit board which has multiple current controls controlled by signals from control lines, and has connections to power lines, connections to the UV source and connections to power source and current return drain on pins. In this embodiment, the pins can be flexible.

In another embodiment, the form encompasses the full head and neck phototherapy system. Again, as above, additional components can include audio speakers, external UV source compatible power supply and house power connector. LEDs or nanostructure-based emitters may be selectively powered to provide specific areas of phototherapy.

Alternatively, a mechanical translating phototherapy system that has a spatial translating UV source loop (or loops) that encircle(s) the user has the advantage of requiring fewer bulbs to treat the same area of skin over a longer period of time. This embodiment has a reduced cost because fewer UVA LEDs or nanostructure UV light emitting devices are required to produce the desired therapy. Either the system (or loop) moves longitudinally with respect to the client, or the client may moves parallel with the axis of the loop, or both. The movement may be manual or it may be power assisted in a manual or automatic control manner. This system can accommodate a standing user or a prone user. The loop(s) can be mounted on a wall or ceiling-mounted track, for example, via a hinge to allow clients to enter and exit the chamber. The UV translucent bed may be acrylic. Translating UV source loops may be comprised of combinations of controllable UVA LEDs or nanostructure UV light emitting devices to be selectively powered depending on position and area requiring tan.

In any UV light exposure application it is recommended for people being exposed to use UV opaque protective eye-wear, and it is recommended for people being exposed to shut the eyelids as much as possible in order to minimize exposure of the retina to UV. It is important to maintain strict observation of the requirement for UV opaque protective eye-wear during operation of phototherapy equipment. Therefore, in one embodiment, special control circuits can be incorporated into the phototherapy systems to prevent powering the UV sources when UV opaque UV opaque protective eye-wear is absent. In addition, training in use of phototherapy equipment is highly recommended.

Some embodiments of the phototherapy devices incorporate combinations of sensors and communication equipment into the phototherapy device to determine if the user has UV opaque protective eye-wear present and worn correctly before allowing the phototherapy system to start emitting UV radiation. This reliable personal phototherapy device incorporates special safety features that identify people and do not allow for over-exposure of any user to UV light over a given time frame. This reliable personal phototherapy device interfaces to a computer terminal with associated software logic and with associated input and output control ports, to provide information such as length of therapy for a each unique user and to provide historical records of user specific phototherapy activities and accounting details.

In an example, a person with UV opaque protective eyewear can be exposed to light therapy in the presence of multiple types of light sources which includes a UVA LED array and/or a nanostructure UV light emitting device alone or in combination with the prior art UV light sources such as high pressure and low pressure fluorescent bulb within a phototherapy chamber. The chamber can optionally possess one or more UV opaque walls, a UV opaque phototherapy chamber door, a ventilation system, a cooling system, a safety switch connected to shut-off controller and/or system controller, a controller communication device, a high voltage ballast (for use with first embodiment of invention or fluorescent bulb and with low voltage LED power supply), and/or an external light output feedback sensor, for use with alternate low voltage embodiment of the present invention and calibration requirements.

The phototherapy systems and devices can be used in conjunction with a payment system associated with, for example, a rental of phototherapy chamber, commercial sales and rental store and of the phototherapy systems as in indoor-phototherapy salons. Battery backup power supplies can be provided for operation of phototherapy equipment and control systems during momentary power outages. A computer based control and communications system for operating the phototherapy salon and associated controllable phototherapy equipment and personal services and communicating with other associated phototherapy salons and home offices via communications lines or via wireless communication system can be incorporated. The communications system may also be adapted to identify and report equipment malfunctions or maintenance needs to a remote location.

As an alternative to phototherapy beds or booths, in some embodiments of the invention, the UV sources are incorporated into articles of clothing, and into cloth, and into flexible forms, and into rigid forms that allow for home phototherapy systems and for personal phototherapy systems such as phototherapy jackets, phototherapy pants, phototherapy suits, phototherapy bags or sacs, phototherapy blankets and phototherapy rooms.

Personal phototherapy systems can be shared by different people at different times. If a personal phototherapy system is shared, it is desirable to have a set of removable UV-translucent garment or liner capable of being washed. A personal phototherapy system that is cleaned in an efficient manner between uses is desirable. A personal phototherapy system with the ability to be cleaned is desirable whether shared or un-shared.

UV light has surface sterilization effects and therefore a personal phototherapy system will to some degree be self-cleaning with regard to certain undesirable bacteria such as mold and mildew. Additionally, UVB and UVC light sources may be incorporated into a personal phototherapy device to produce a higher degree of sterilization when operated in a special cleaning mode without the presence of a user.

The clothing may be in the form of full or partial body phototherapy apparel. For example, apparel can avoid golfer's tan by allowing full body exposure to the light while still providing privacy where the outer layer of the apparel is opaque. The apparel can be made of material that contains a UV blocking or reflecting component positioned to keep the UV light in the apparel. The apparel can be lined with a removable layer or a first inner layer can be a layer in between the outer and inner layer that contains the UV sources and circuit board and the circuitry and cooling and controlling components. A UV translucent inner layer comes in contact with the client. For sanitary reasons the inner layer is preferably used exclusively by a single client and/or can be washed. This inner fabric will be completely or partially transparent to UV light. The inner fabric will also be able to diffuse the UV light in a manner that will allow the client to receive a consistent tan over the surface of the body. Controls selectively control the UV sources to be energized in a desired pattern. This desired pattern may be saved and recalled automatically through the registration and control system connected to controlled power lines and a control line. A UV opaque zipper or other fastener can be used to get into the full body tanning apparel and limit the amount of UV radiation emitted. This embodiment of the invention will allow tanning slowly over a period of time preferably while sleeping. Slow tanning may be less stressful on the skin. Tanning apparel and sleeping bags may be used to slow down the tanning process, reduce the required light flux and can tan in a comfortable environment. Cooling systems can also be controlled by control system through control wires. External UV source compatible power supplies and house power connectors can be incorporated into the device.

The apparel can have a layer of partially or fully UV opaque material, inside the inner layer of the full body tanning apparel next to the body covering parts of the client that require no UV exposure. Alternatively, the client can attach a patch to the skin to protect it from UV exposure. The use of partially or fully UV opaque filters results in a controlled tanning pattern without the need for granular control of the UV source.

Of course, multiple connections and controllers over various parts of the full body phototherapy apparel, can be used rather than a single controller or connector, whether the chamber is made of fabric, is flexible or rigid.

Modular selective phototherapy apparel allows selectable patterns for phototherapy. Modular and selective phototherapy is useful in medical cases such as a person with a medical skin condition (e.g., psoriasis) that requires a prescribed light therapy as directed by a physician or other medical person or medical therapist. In this embodiment, the module connectors are connected to a common controller at the phototherapy apparel edge. An alternate design uses external connectors. Multiple two-dimensional components connected into three-dimensional assemblies are useful building block components for modular phototherapy apparel.

Various shapes of modular phototherapy apparel can be readily envisioned, including, for example, a torso, leg, foot, arm, scalp, pants, shirt and hat. The shapes can be interconnectable pieces of phototherapy apparel to build a complete or partial modular phototherapy suit. Arbitrary numbers of connector, arbitrary types of connectors, arbitrary shapes of components, and arbitrary materials of components, and arbitrary orientations of connectors allow for arbitrary phototherapy devices to be constructed.

A curved three-dimensional modular fabric component for completing power and control signal connections between phototherapy apparel components, with two sides having male style connector power pins and male style communications connector and two sides with female style hollow power connectors and female style communications connector. Alternatively, a curved three-dimensional modular fabric component with one, two or three sets of male connectors which would represent an end component or corner of the fabric can be made. Not shown is the curved three-dimensional modular fabric component with one, two or three sets of female connector which would represent an end component in the fabric.

Two-dimensional components used to build three-dimensional assemblies connections from one segment of clothing to another for power and control signals can be designed to keep electromagnetic interference to a minimum.

A three-dimensional modular fabric component, such as a box component, for completing power and control signal connections between phototherapy apparel components, with two sides having male style connector power pins and male style communications connectors and two sides with female style hollow power connectors and female style communications connectors can be conveniently used. One or more of each component can be used. Not shown is one side with quartz or other UV translucent material to allow UV light to reach the skin. Arbitrary numbers of connector, arbitrary types of connectors, arbitrary shapes of components, and arbitrary materials of components, and arbitrary orientations of connectors allow for arbitrary tanning devices to be constructed.

Illustrative Phototherapy Designs and Parameters

The present discussion is provided to illustrate various non-limiting system designs and parameters that may be adopted for carrying out some specific exemplary types of phototherapies in accordance with the present invention.

It should be noted that the systems and devices of the present invention are particularly well suited for use in phototherapies generally, and the phototherapies listed below in particular, because they make it possible to adjust the overall, combined, resulting spectral distribution which may be composed of one or more component spectral distributions, each of which may be programmatically controlled to vary over time as needed during a phototherapy session (e.g., during the treatment of lupus). In addition, the present system and devices provide either continuous spectral distributions or spectral distributions having discrete atomic spectral lines at selected, well-defined locations. Using the latter embodiment, the location of the lines may be selected to provide more intense phototherapy where it is needed or wanted. This is in contrast to mercury vapor lamps and to phosphor converted fluorescent mercury vapor lamps which inevitably emit some discrete atomic spectral lines at naturally occurring, fixed (i.e., not selectable) locations. Therefore, using these lamps it is not possible to carefully tailor the location of the regions of intense phototherapy.

Lupus Phototherapy:

Both the UV LED and nanostructure-based systems and devices provided herein may be used in the treatment of lupus. For example, the invention provides methods of treatment wherein UV light provided from at least one light emitting diode or from a nanostructure UV light emitting device, of the type described herein, is directed onto the skin of a human subject having lupus. Typically, the systems and devices designed for lupus phototherapy will be tailored to expose the entire patient, or a significant portion of the patient to the UV light.

The treatment of lupus with UV light generated by mercury vapor based light sources and long wavelength (UVA-1) passing light filters is known and is described in "Reversal of brain dysfunction with UV-A1 irradiation in a patient with systemic lupus," Lupus. 2003; 12(6):479-82; "Ultraviolet-A1 (340-400 nm) irradiation therapy in systemic lupus erythematosus," Lupus. 1996 August; 5(4):269-74; "Longtern ultraviolet-A1 irradiation therapy in systemic lupus erythematosus," J. Rheumatol. 1997 June; 24(6):1072-4; "Ultraviolet A1 (340-400 nm) irradiation and systemic lupus erythematosus," J Investig Dermatol Symp Proc. 1999 September; 4(1):79-84. Review; "Ultraviolet-A1 irradiation decreases clinical disease activity and autoantibodies in patients with systemic lupus erythematosus," Clin Exp Rheumatol. 1994 March-April; 12(2):129-35, the entire disclosures of which are incorporated herein by reference. Suitable phototherapy treatment conditions, including wavelengths, intensities and exposure times are described in these references. In some preferred embodiments, the UV radiation having a wavelength of about 400 to about 340 nm is employed.

Psoriasis Phototherapy:

Both the UV LED and nanostructure-based systems and devices provided herein may be used in the treatment of psoriasis. For example, the invention provides methods of treatment wherein UV light provided from at least one light emitting diode or from a nanostructure UV light emitting device, of the type described herein, is directed onto the skin of a human subject having psoriasis.

Desirable phototherapy treatment parameters for psoriasis include exposure to a narrow band emission peaking at or between 312 nm and 311 nm. Because the nanostructure UV light emitting devices are capable, through various manufacturing processes, of providing highly controlled spectral distribution emission bands, including broad bands and very narrow bands which can range from widths of 200 nm to vanishingly narrow, nearly discrete bands they are well suited for this application. Therefore the nanostructure UV light emitting devices can be designed to deliver a narrow band of light peaking between 312 nm and 311 nm. This represents an improvement over psoriasis phototherapies that use mercury vapor lamps, because such lamps are only capable of delivering a discrete spectral line at 313 mm, but in the ranges with peaks between 311 nm or 312 nm, which are the preferred wavelengths for psoriasis phototherapy.

In these embodiments the UV chambers used in the phototherapy systems and devices may be tailored to conform to and provide UV irradiation to only that part of the body suffering from the condition. For example, the chambers may be tailored to irradiate only an arm, a leg or the face of the subject.

UV phototherapy for the treatment of psoriasis is described in U.S. Pat. No. 6,436,127, the entire disclosure of which is incorporated hereby reference. This reference includes additional descriptions of suitable phototherapy parameters, such as wavelength ranges, power and duration.

Hair Growth Phototherapy:

Both the UV LED and nanostructure-based systems and devices provided herein may be used to promote hair growth or regrowth on a human subject. For example, the invention provides methods of treatment wherein UV light provided from at least one light emitting diode or from a nanostructure UV light emitting device, of the type described herein, is directed onto the skin of a human subject desiring hair growth or regrowth. The UV light may be used in conjunction with a hair growth assistance chemical, such as minoxodil which undergoes a hair growth-stimulating photochemical reaction when exposed to the UV radiation.

In these embodiments the UV chambers used in the phototherapy systems and devices may be tailored to conform to and provide UV irradiation to only that part of the body where hair growth of regrowth is desired. For example, the chambers may be tailored to irradiate only the scalp of a subject. In one such embodiment, the chamber may take on the form of apparel, such as a helmet or hat, that the subject can wear as a personal phototherapy device.

By way of illustration only, one specific example of a system that may be used to stimulate hair growth is described as follows. This embodiment incorporates an LED based hair growth assistance means, wherein said LED based hair growth assistance means is comprised of combinations of components including but not limited to a hair growth assistance light source means (typically a plurality of LEDs with one or more wavelength including but not limited to UV light emitting diodes with wavelength of 395 nm), a light mixing means (when more than a single wavelength LED is incorporated), a hair growth assistance enclosure means, a hair growth assistance fit detection means (including proximity safety switches on said hair growth assistance enclosure means and on said UV eyewear protection means to determine proper fit of both the UV protection eyewear and the hair growth assistance enclosure), a hair growth assistance power supply means (low voltage with at least one national certification or international certifications, for example in the USA a UL approved rating), a hair growth assistance electric current overdrive control means (for reducing the required number of LEDs), a hair growth assistance light measurement means (used to determine imminent failures or feedback to current control means in the case of reduced luminous power over time), a hair growth assistance memory (to determine life and usage patterns), a hair growth assistance microcontroller (e.g. MC68CH11 with ROM, RAM and FLASH), hair growth assistance microcontroller operating programs, a hair growth assistance active junction temperature environmental control means, a hair growth assistance light source cooling means, a hair growth assistance control means (with operation lockout features), a hair growth assistance communications means (for connecting proximity sensors), a hair growth assistance timer means (with maximums and responsive to logic in the case of a poor fit restart of a single session), a battery (for portable operation) useful for the purpose of stimulating hair growth with reduced hazards. Said UV LED includes but is not limited to UV light emitting diodes, wherein UV light emitting diode includes but is not limited to UV-395-TO92 manufactured by Bivar Corp, Irvine, Calif., USA, to NSHU550A manufactured by Nichia USA, and to LC503MUV1-30Q a 5 mm t-1¾ package from Marktech Optoelectronics, Menands, N.Y., USA.

Teeth Whitening Phototherapy:

Both the UV LED and nanostructure-based systems and devices provided herein may be used to whiten teeth. For example, the invention provides methods of treatment wherein a teeth whitening agent, such as carbamide peroxide, is applied to a subject's teeth and UV light provided from at least one light emitting diode or from a nanostructure UV light emitting device, of the type described herein, is directed onto the whitening agent-coated teeth. This teeth whitening phototherapy could be done by a dentist or in a tanning salon. UV to blue light having wavelengths of about 340 nm to about 700 nm, and specifically about 395 to about 410 are well suited for use in teeth whitening phototherapies.

In these embodiments the phototherapy systems and devices may be tailored to conform to and provide UV irradiation to the teeth of the patient. In one such embodiment, the device may take on the form of a mouth guard or dental retainer, that the subject can wear as a personal phototherapy device. Such devices would irradiate the teeth from inside the mouth, preferably from the direction of the lips toward the teeth. Alternatively, the device may include a one or more external UV LEDs or nanostructure UV light emitting device and a brace for holding the subjects lips and/or tongue away from the teeth in order to avoid unnecessary exposure of the lips and tongue to the radiation. Such braces are well known in the dental arts.

UV phototherapy for teeth whitening is described in U.S. Patent Application Publication No. 2004/0076926, issued to Baughman, the entire disclosure of which is incorporated by reference. This reference describes suitable phototherapy parameters, including wavelengths, power and duration, as well as mouthpieces that may be adapted to provide internal UV phototherapy devices in accordance with the present invention.

By way of illustration only, one specific example of a system that may be used to whiten teeth is described as follows. This embodiment incorporates an LED based teeth whitener means, wherein said LED based teeth whitener means is comprised of combinations of components including but not limited to a teeth whitener light source means (typically a plurality of LEDs with one or more wavelength including but not limited to UV light emitting diodes with wavelength of 395 nm), a light mixing means (when more than a single wavelength LED is incorporated), a teeth whitener enclosure means (with substantially opaque walls and with translucent interior and with one or more UV translucent openings arranged so as to protect skin and gums while exposing teeth to phototherapy), a teeth whitener fit detection means (including proximity safety switches on said teeth whitener enclosure means and on said UV eyewear protection means to determine proper fit of both the UV protection eyewear and the teeth whitener enclosure), a teeth whitener power supply means (low voltage with at least one national certification or international certifications, for example in the USA a UL approved rating), a teeth whitener electric current overdrive control means (for reducing the required number of LEDs), a teeth whitener light measurement means (used to determine imminent failures or feedback to current control means in the case of reduced luminous power over time), a teeth whitener memory (to determine life and usage patterns), a teeth whitener microcontroller (e.g. MC68CH11 with ROM, RAM and FLASH), teeth whitener microcontroller operating programs, a teeth whitener active junction temperature environmental control means, a teeth whitener light source cooling means, a teeth whitener control means (with operation lockout features), a teeth whitener communications means (for connecting proximity sensors), a teeth whitener timer means (with maximums and responsive to logic in the case of a poor fit restart of a single session), a battery (for portable operation) useful for the purpose of teeth brightening teeth with reduced hazards. Wherein said dental light directing means is commercially available and sold under the name "Twilight Teeth" UV light catchers used in combination with UV LED for the adaptation of the commercially available tooth brightener, where said UV LED includes but is not limited to UV light emitting diodes, wherein UV light emitting diode includes but is not limited to UV-395-TO92 manufactured by Bivar Corp, Irvine, Calif., USA, to NSHU550A manufactured by Nichia USA, and to LC503MUV1-30Q a 5 mm t-1¾ package from Marktech Optoelectronics, Menands, N.Y., USA.

Temperature Dependent Wavelength Shifting for Phototherapy Applications

Another aspect of the present invention provides a means of varying the nominal wavelength of emitted light by heating and/or cooling the UV light emitting LEDs. This is useful for obtaining wavelengths other that the nominal wavelength of the LED which would be required for particular phototherapy prescriptions, such as lupus phototherapy where it is desirable to vary the wavelength of the light during treatment.

In LEDs the most common typical wavelength shifting observed is referred to as a red-shift, wherein the typical shift of the wavelength of emitted light is toward longer wavelengths. In light emitting diodes that do not have the benefit of the present invention the temperature of the semiconductor junction gets hotter with increased electric current and the forward voltage drop in the active junction increases resulting in the wavelength shift.

Operating LEDs at lower than normal temperature is useful in shifting the wavelength of the emitted light to a range that is not emitted under normal operating conditions, which includes but is not limited to a controlled shift toward shorter wavelength, herein referred to as a blue-shift. Shifting the emitted output of the LEDs is useful to implement phototherapies that require certain wavelengths that are not normally available from the LEDs.

Some embodiments of the present invention incorporate combinations of LED cooling means and LED heating means useful for controlling the temperature of the LED active junction in an arbitrary dynamic pattern responsive to the output of a phototherapy control algorithm.

Cooling of LEDS may be carried out using a thermal insulation means in proximity to cold compressed refrigerant piping means for the useful purpose of keeping said cold compressed refrigerant piping to said LEDs and in particular the heat generating mass of the LED including the active junction of the LED. Any suitable cooling fluid, including water or alcohol based fluids may be used to cool the LEDs. LED cooling is described in greater detail below.

Multiplexing Phototherapies

Still another aspect of the invention provides systems, devices and methods for phototherapy that use one UV source (i.e., at least one UV emitting LED or a nanostructured UV light emitting device) to irradiate multiple body parts or multiple people. These systems, devices and methods may find use is a broad variety of phototherapy applications, including tanning, lupus phototherapy, psoriasis phototherapy, teeth whitening and hair growth phototherapies. Some such devices, including those that have controllable mirrors or mechanically translating UV sources have already been described. Other such systems are described here.

In some embodiments, the systems, devices and methods include a combination of reflective surfaces or optical pipes to direct light from a horizontal light due to vapor phase changes to any direction of light. In some embodiments a wall of a device (i.e., a phototherapy chamber wall) has a light modifying means in order to redirect the light in a manner that distributes the light according in a manner consistent with a indoor tanning mode or a phototherapy mode. One example of a light modifying means is a lens. Other light modifying means include, but are not limited to, reflective surfaces, optical lens, and light pipes.

A further embodiment of the present invention incorporating said light provisioning means, a plurality of said light wave guide means, and a light directing means, for the useful purpose of provisioning light from remote sources relative to the phototherapy chamber, on the order of 100 feet or less. The useful purposes of provisioning light remotely includes but is not limited to the purpose of time sharing the light provisioning source, the purpose of more effective cooling at a remote location, and for the purpose of reducing the number of components in a multiple phototherapy chamber enterprise by time sharing the LED array. Wherein said light directing means switches the direction of light from one wave-guide to another depending on a control system which manages the sharing of the light provisioning means.

A further embodiment of the present invention incorporates a plurality of light provisioning means, a plurality of said light wave guide means, and a plurality light directing means, for the useful purpose of provisioning light from remote sources relative to the phototherapy chamber, on the order of 100 feet or less. The useful purposes of provisioning light remotely includes but is not limited to the purpose of time sharing the light provisioning source, the purpose of more effective cooling at a remote location, and for the purpose of reducing the number of components in a multiple phototherapy chamber enterprise by time sharing the LED array. Wherein said light directing means switches the direction of light from one wave-guide to another depending on a control system which manages the sharing of the light provisioning means.

Yet another embodiment of the present invention incorporates said light wave guide means wherein said light waveguide means are comprised of light transmitting means including but not limited to light collecting means, reflective mirrors, and reflective tubes, which may be hollow reflective tubes. The reflective tubes may be fiber optic tubes, comprised of materials including but not limited to glass, plastic, UV transparent fluid.

Thermal Management

Another aspect of the present invention provides systems and methods for achieving high levels of thermal efficiency in devices, including both phototherapy and general lighting devices, that use the UV LEDs and nanostructure UV light emitting devices provided herein. In this aspect of the invention cooling methods are used to more effectively transfer heat from light emitting diodes to the ambient environment by introducing liquids, such as a the cooling fluid, near the active junction of the light emitting diode to transfer heat from the LEDs to the ambient environment. These cooling methods may use one or more types of cooling, including immersion cooling, liquid cooling and evaporative cooling.

A low active junction temperature (within the manufacturer's specifications) is useful because it allows the light emitting diode type LED to be either overdriven with electric current (described below) while maintaining the rated life of the LED, or to extend the life of the LED while maintaining electric current under rated maximums.

The systems and methods are described in detail in U.S. Provisional Patent Application No. 60/552,018, (e.g., on pages 25-43) the entire disclosure of which is incorporated herein by reference. A more abbreviated description is provided here.

The methods may be used to cool various electronic components, including encapsulated LEDs and bare LED dies. For example, the methods are used to cool open framed light emitting diodes. Said open framed light emitting diodes are not encapsulated. The use of open framed UV light emitting diodes reduces the manufacturing tooling costs associated with custom chip on board technology while still allowing for the direct contact immersion cooling of said LED die. These open framed UV light emitting diodes may be obtained by diverting open framed light emitting diodes out of an industry standard LED manufacturing process after the wire bonding manufacturing process and before the encapsulation manufacturing process is applied.

A further embodiment of the present invention incorporates a coating on said LEDs to protect said LEDs from the chemical reaction potential of the cooling fluid and the force of said cooling fluid flow. The coating is preferably a highly transparent coating and, in the application of indoor tanning or other phototherapies, a highly UV transparent coating. The coating may be comprised of materials including, but not limited to, silicone compounds, to silicone sealant, and to epoxies.

In carrying out the cooling methods, the cooling fluid may be directed near and/or between LEDs or LED chips. The cooling fluid may be directed using a variety of conduits including, but not limited to tubing, micro-channels, Venturi tubes, expansion valves, and porous substrates. The cooling methods may be carried out using a built-in cooling source means which may be an integral component of a phototherapy chamber or a general lighting device. In the former instance, the cooling source may be used to cool the UV light source in the chamber, as well as the chamber itself. Typically, the cooling source will include means to transport (including directing and propelling) cooling fluid to the proximity of the active junction of at least one light emitting diode and insulating means to keep the cooling fluid cold during transport. In addition, the cooling source may include a cooling control system responsive to inputs, including but not limited to estimated active junction temperature, and to measured active junction temperatures.

Water is one non-limiting example of a cooling fluid that may be used in accordance with the present invention. Other suitable cooling liquids include mixtures of alcohol (e.g., isopropyl alcohol) and water, air, perfluorocarbons and silicone oils.

If the UV source to be cooled is part of a phototherapy system and the cooling fluid flows in front of the light source, the cooling fluid is desirably optimized for the requirements of the particular phototherapy being conducted. For example, the light transmission properties of the cooling fluid may be chosen to be high in transmission of the wavelengths useful in said phototherapy and low in transmission of light that is prohibited or undesirably in said phototherapy. Thus, for indoor tanning the wavelength of transmission would desirably be limited to 400 nm to 300 nm, and for lupus therapy the wavelength of transmission would desirably be limited to 400 nm to 340 nm.

Perfluorocarbon cooling fluids are well suited for use as coolants in UV light emitting devices because they are generally good at transmitting UV light. In some embodiments the perfluorocarbon cooling fluid has a relatively low atomic mass and a boiling temperature between 30 and 40 degrees Celsius at 1 atmosphere pressure. An example of such a chemical has boiling point of 29 degrees Celsius, has a molecular weight of 288, is labeled PP50, and is manufactured by F2 Chemicals Ltd (Lee Lane, Lea Town, Nr Preston, PR4 ORZ, UK). In other embodiments, the perfluorocarbon cooling fluid has a relatively high molecular weight and boils above 130 degrees Celsius at 1 atmosphere (ATM). An example of such a chemical has a elemental mass of 462 is labeled PP6 and is manufactured by F2 Chemicals Limited (Lee Lane, Lea Town, Preston. PR4 ORZ, United Kingdom).

In some embodiments, the cooling fluid undergoes pool boiling or nucleate boiling. This may be advantageous because the hottest points of the LED are the places where the boiling occurs and are also where the most cooling is needed. In other embodiments, the cooling fluid is a heavier cooling fluid that boils at a temperature and pressure well above those found in proximity to an LED, e.g., PP6, manufactured by F2 Chemicals Ltd.

Magnetic and paramagnetic cooling fluids may also be used. For example, the invention may incorporate a magnetic fluid means, including but not limited to a magnetic fluid wherein, said magnetic fluid has elements including, but not limited to, iron and/or nickel. Additional magnetic fluids that comprise a magnetic material may be selected from the group consisting of Cr, Mn, Fe, Co, Ni, V, La, Ce, Pr, Nd, Pm, Sm, Eu, Gd, Tb, Dy, Ho, Er, Tm, Yb, Ac, Th, Pa, U, Ne, Pu, Am, Cm, Bk, Cs, Es, Fm, Md, No, Lr, Tb—Fe, Gd—Fe, Nd—Fe, Gd—Co, Er—Ni, U—Co, $Fe_4N$, $Fe_5N$, and $Fe_3O_4$. Or the invention may incorporate a paramagnetic fluid means including, but not limited to, a paramagnetic fluid wherein, a paramagnetic material comprises a paramagnetic material selected from the group consisting of silica, alumina, yttria, zirconia, hafnia, titania, niobia, Ag, Al, Cu, Si, Au, Pt, Pd, Rh, Ru, Mo, Nb, Ta, W, Ti, V, Zr, Hf, Y, Re, Ir, Ga, In, Sn, Pb, Zn, Cd, Hg, Ag—Al, Cu—Al, Pd—Ag, $Al_2O_3$, $SiO_2$, BN, NbN, TaN, TiN, $Fe_2O_3$, CoO, $Ni_3Al$, and FeAl.

Magnetic elements may also be combined with non-magnetic fluids to impart magnetic characteristics. For example, a perfluorocarbon fluid with an integral magnetic element such as iron, nickel or a ferrofluid, ferroperfluorocarbon fluid, including the Flutec Ltd, fluid, Ferrofluid, may be used as a cooling fluid.

In one cooling device, the magnetic or paramagnetic fluid means passes through a micro coil which creates an electric field potential in the coil as the magnetic or paramagnetic fluid comes to magnetic saturation. Magnetic saturation in the magnetic or paramagnetic fluid decreases after passing through the non-energized micro coil and entering the open ventricle of a micro stirling engine wherein there is cooling due to the magnetic interactions of the magnetic or paramagnetic fluid that begins to randomize from the heat contained in a cold source within the magnetic forces between the magnetic or paramagnetic fluid. Each time the magnetic or paramagnetic fluid passes between thermodynamic chambers the magnetic energy will either be absorbed or allowed to pass through depending on the controlled state of a current control means.

A further embodiment of the present invention regenerates electricity by operating a current control means in a second mode where the heat of an electrically powered first LED produces mechanical pressure in a first magnetic fluid chamber forcing said magnetic fluid through a micro coil aperture into a second magnetic fluid chamber which creates an electric current potential useful for generating electric energy. As the ferromagnetic fluid passes through the micro coil the ferromagnetic fluid is cooled. At the end of the cycle the first LED is no longer powered and a second LED in contact with second magnetic fluid chamber transitions from no power to power which heats the magnetic fluid in the second chamber and forces the magnetic fluid back into said first magnetic fluid chamber in combination with a current switch receiving current from the micro coil which rectifies the current through the coil in the opposite polarity relative to the first cycle which is useful for power generation. In addition to regenerating electric current from heat the fluid flow cools the LED surface providing longer life at overdriving conditions (discussed below).

A further embodiment of the present invention incorporates a means to convert power in the form of heat transfer into useful work power such as electricity and or mechanical movement, such as fluid flow. This conversion process may be in the form of a Carnot cycle, Stirling cycle, Brayton cycle, Ericsson cycle or a thermodynamic cycles of a Stirling engine, including a micro-Stirling engine, wherein the resultant work power is in the form of electric current at a active junction electric voltage potential and used to power the LEDs or to operate other device components, such as fans and pumps.

Other components that may be included in the systems include, but are not limited to, a pneumatic force imparting means to create forced convection in the cooling fluid and to increase heat transfer fluid force vectors beyond the force vectors provided by the natural convection; and an ultrasonic frequency means to effect the reduction of additional barriers of heat flow near the surface of said LEDs.

Overdriving LEDs

The cooling methods of the present invention allow the LEDs to have increased heat transfer which allows operation at a lower active junction temperature for a given current, as compared to the prior art which relied on heat transfer through air. The maximum allowable current through each LED will be increased as a result of the increased heat transfer and a lower active junction temperature, thereby allowing each LED to produce more photons. The increase in the quantity of emitted photons per LED die allows for a reduction in the total number of LEDs used for a given application (e.g., to create a phototherapy chamber for a desired session time). The reduction in the total number of LEDs lowers the cost of said application. The mode of operation wherein more electric current is applied to the LED that the rated maximum is referred to as overdriving LEDs.

It should be noted that overdriving the LEDs for short periods of time and overdriving the LEDs with short duty cycles over long periods of time will not require a cooling system under normal ambient conditions to achieve a rated life of the LED array. Unfortunately, overdriving the LEDs for short periods of time and overdriving the LEDs with short duty cycles over long periods of time are not useful conditions of operating the LED array for the purposes of many phototherapy procedure including but not limited to indoor tanning, and lupus therapy. An example of a phototherapy requiring additional LEDs is the condition where an area of skin is to be treated and the wavelength of the emitted light is required to be within a range that is only possible to achieve with LEDs that are operated with short duty cycles.

Power Sources

Figure 12:
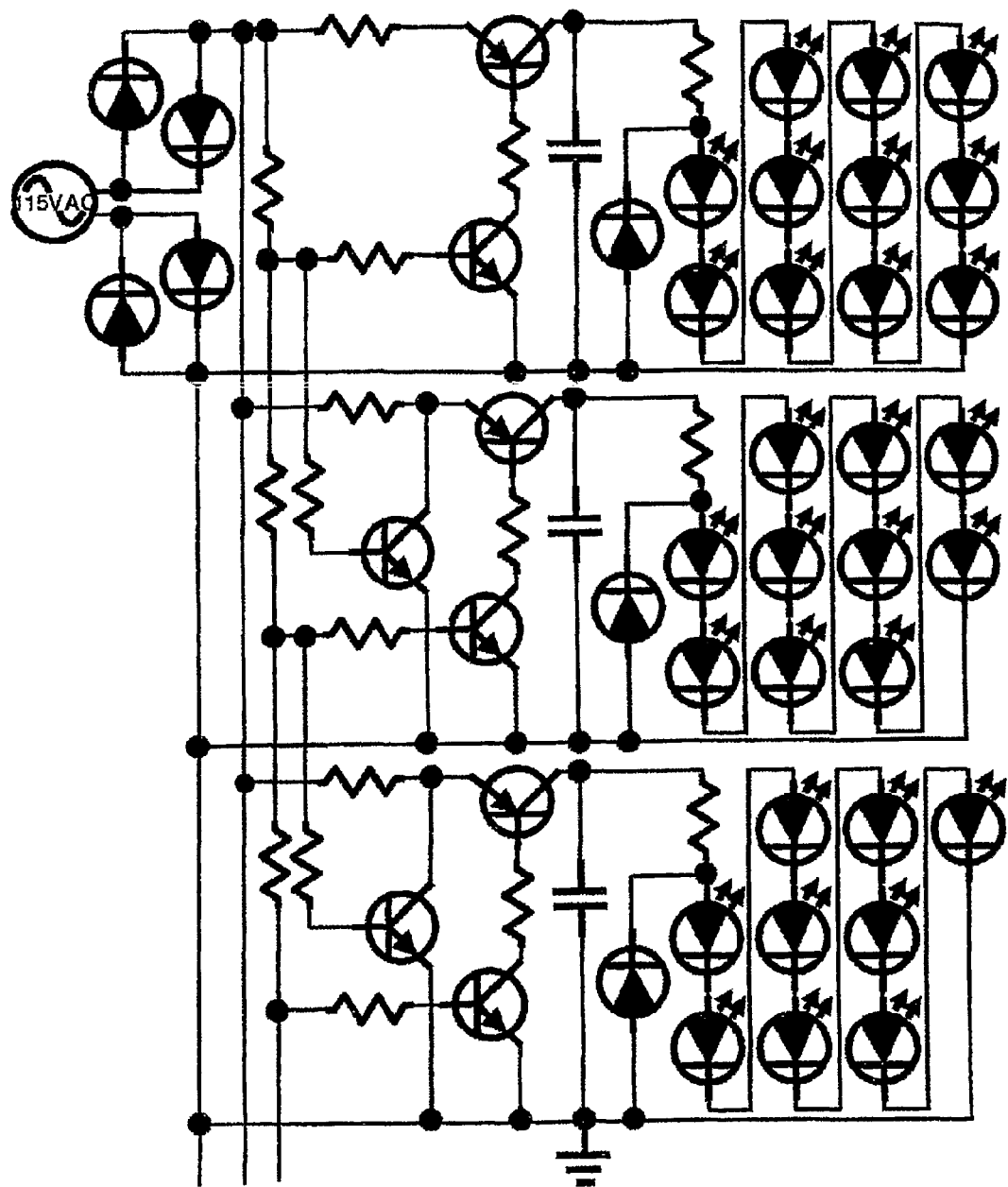
FIGS. 12-15 show various power sources that may be used to power the LEDs in the systems and devices described herein.
Figures 13A, 13B, 13C:
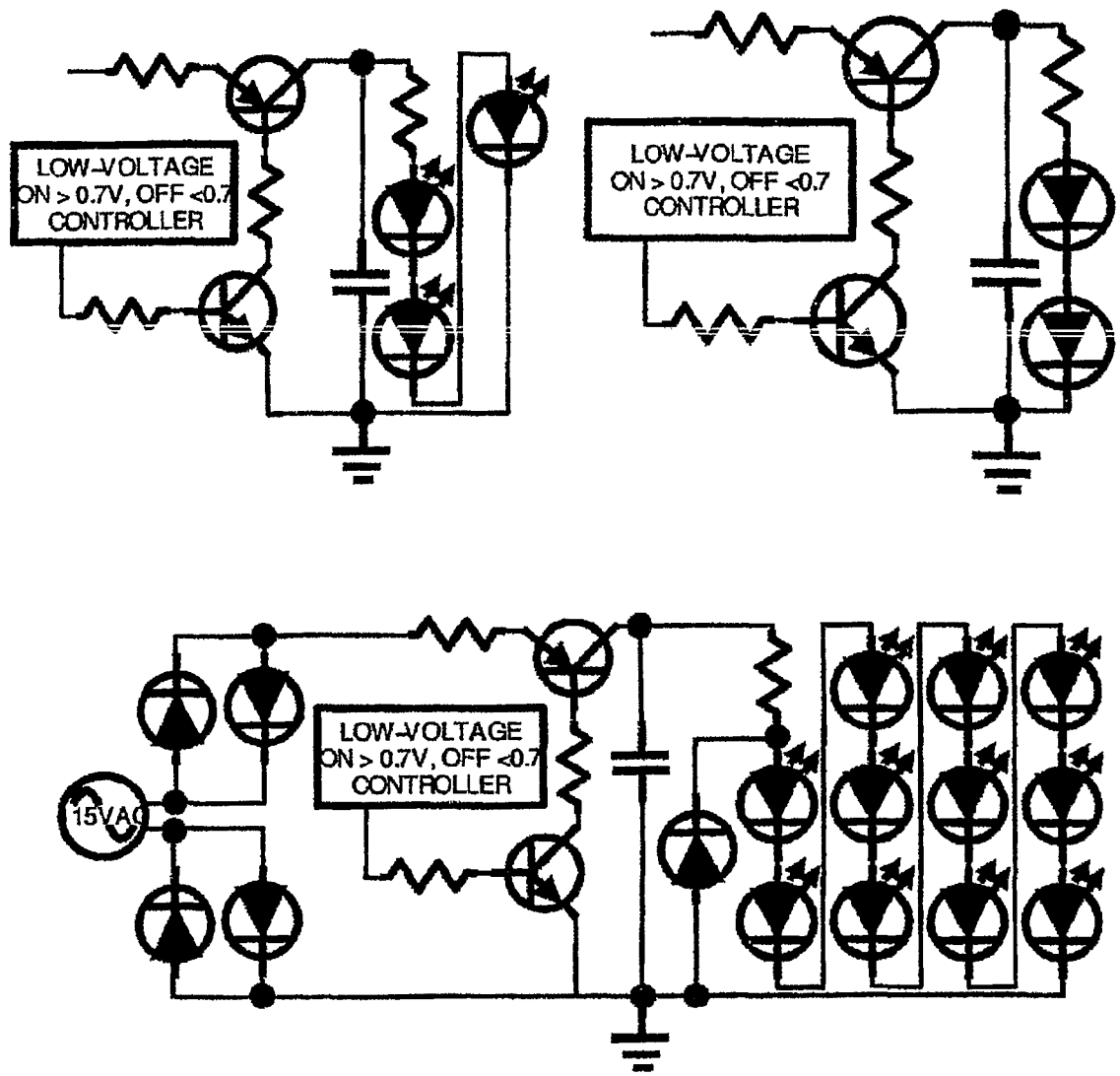
Figure 14:
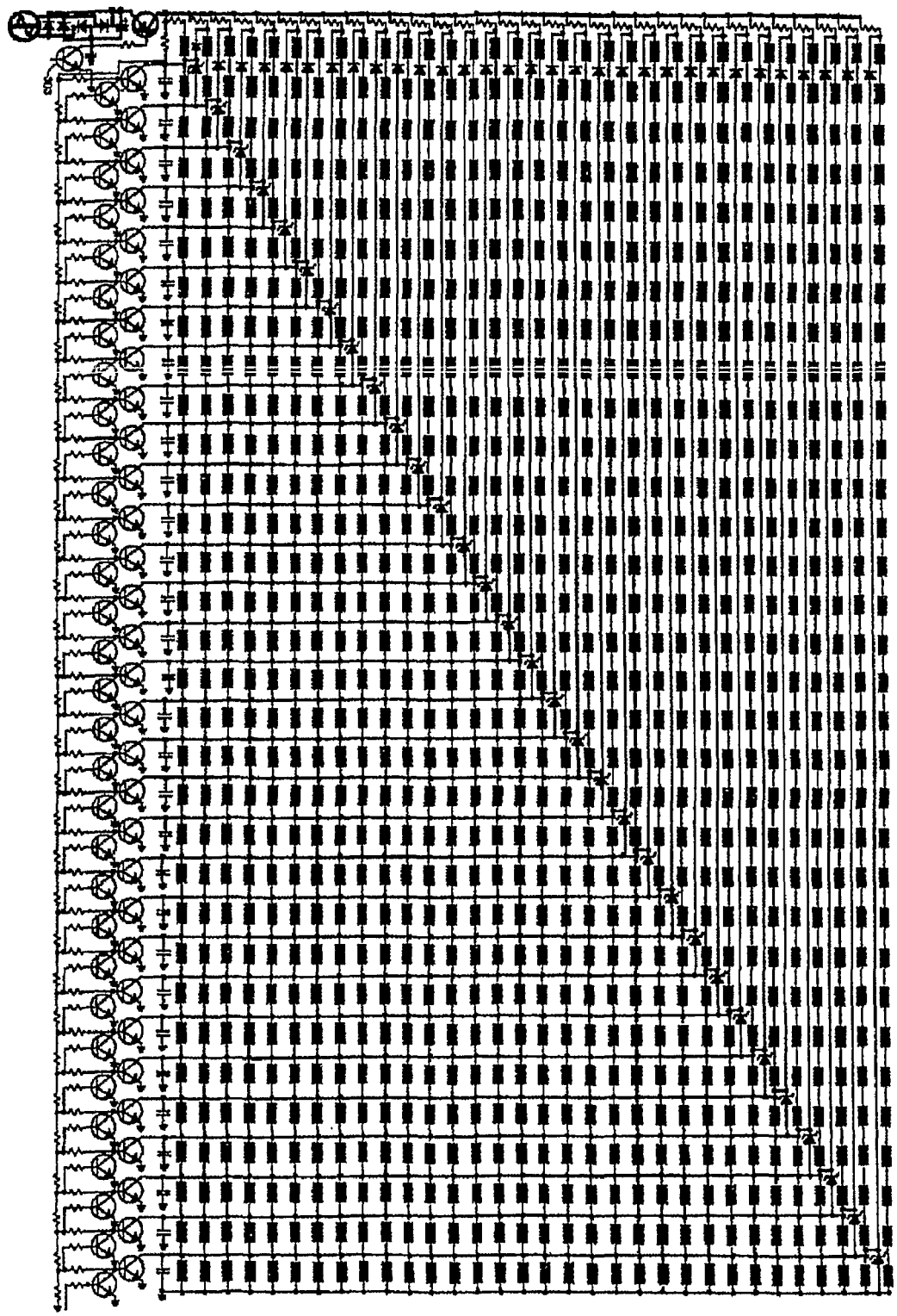
Figure 15:
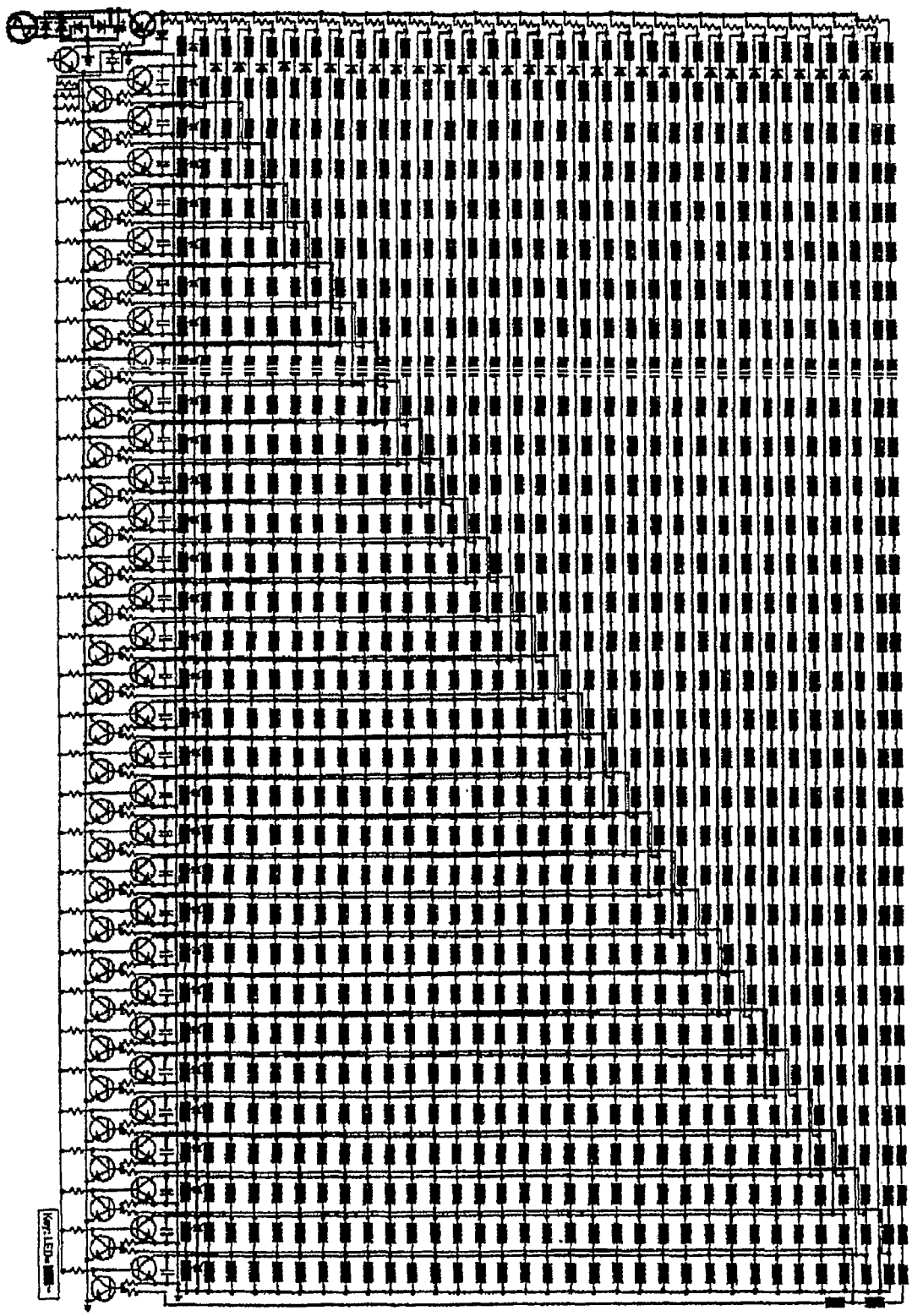

A final aspect of the invention provides various circuits that may be used to power the LEDs used in the present systems and devices. These circuits are depicted in FIGS. 12 through 15. FIG. 12 shows a basic circuit for use in powering LEDs. FIGS. 13a, 13b, and 13c show variations in the circuit. FIG. 14 shows a direct line voltage power supply that has a useful near unity power factor LED transfer function which is useful to remove the need for a switching power supply utilizing resistor ladder network to creates bias for transistors. FIG. 15 shows a direct line voltage power supply that has a useful near unity power factor LED transfer function which is useful to remove the need for a switching power supply utilizing resistor ladder network to creates bias for transistors. Field effect transistors may also be used in equivalent circuits. Also, microcontrollers with analog to digital and digital to analog converters may be used in addition to or in place of the resistor ladder networks shown in the figures.

U.S. Provisional Patent Application No. 60/473,237, filed May 24, 2003 and U.S. patent application Ser. No. 10/714,824 are hereby incorporated by reference in their entirety.

The foregoing description of the invention has been presented for purposes of illustration and description. It is not intended to be exhaustive or to limit the invention to the precise form disclosed, and modifications and variations are possible in light of the above teachings or may be acquired from practice of the invention. The drawings and description were chosen in order to explain the principles of the invention and its practical application. It is intended that the scope of the invention be defined by the claims appended hereto, and their equivalents.

What is claimed is:

1. A method for conducting phototherapy, comprising:
   receiving a human subject suffering from psoriasis in a chamber adapted for psoriasis phototherapy,
   providing UV light from a light emitting device comprising a nanostructure light emitting device or a light emitting diode onto the human subject;
   wherein:
      the light is provided onto a skin of the human subject having psoriasis, and the light emitting device emits UV light in having an emission peak at or between 312 and 311 nm and a full width half maximum of about 0.1 to 2 nm suitable for performing psoriasis phototherapy.

2. The method of claim 1, wherein the chamber comprises a bed or a booth.

3. The method of claim 1, wherein the light emitting device comprises at least one of a nanoparticle or a nanowire nanostructure light emitting device.

4. The method of claim 3, further comprising:
   providing UV excitation radiation of a first peak wavelength from a UV excitation source to the light emitting device; and
   emitting the UV light having a second UV peak wavelength longer than the first peak wavelength from the light emitting device in response to the provided UV excitation radiation.

5. The method of claim 1, wherein the light emitting device comprises a light emitting diode.

6. The method of claim 1, wherein the UV light emitted by the light emitting device has a bell curve characterized by an emission peak at or between 312 and 311 nm and a full width half maximum of about 0.1 to 2 nm suitable for performing psoriasis phototherapy.

7. The method of claim 1, further comprising adjusting the wavelength range of the light during the phototherapy.

* * * * *